(12) United States Patent
Liao

(10) Patent No.: US 6,423,751 B1
(45) Date of Patent: *Jul. 23, 2002

(54) UPREGULATION OF TYPE III ENDOTHELIAL CELL NITRIC OXIDE SYNTHASE BY AGENTS THAT DISRUPT ACTIN CYTOSKELETAL ORGANIZATION

(75) Inventor: James K. Liao, Weston, MA (US)

(73) Assignee: The Brigham and Women's Hospital, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/115,387

(22) Filed: Jul. 14, 1998

(51) Int. Cl.[7] .......................... A61K 31/15; A61K 38/00; A61K 38/16; A01N 37/18
(52) U.S. Cl. .................. 514/640; 514/211.08; 514/218; 514/253; 514/253.04; 514/253.05; 514/253.06; 514/253.07; 514/279; 514/307; 514/309; 514/369; 514/411; 514/220; 514/602; 514/603; 514/604; 514/443; 514/565; 514/2; 514/8; 514/44; 424/130.1; 424/142.1; 424/152.1; 424/172.1
(58) Field of Search ............................... 514/411, 640, 514/309, 2, 8, 44, 218, 220, 253.04, 253.05, 253.06, 253.07, 307, 369, 443, 565, 211.08, 253, 279, 602, 603, 604; 424/130.1, 142.1, 152.1, 172.1

(56) References Cited

U.S. PATENT DOCUMENTS

| | | | |
|---|---|---|---|
| 3,983,140 A | | 9/1976 | Endo et al. |
| 4,231,938 A | | 11/1980 | Monaghan et al. |
| 4,346,227 A | | 8/1982 | Terahara et al. |
| 4,351,844 A | | 9/1982 | Patchett et al. |
| 4,444,784 A | | 4/1984 | Hoffman et al. |
| 4,448,784 A | | 5/1984 | Glamkowski et al. |
| 4,450,171 A | | 5/1984 | Hoffman et al. |
| 4,499,289 A | | 2/1985 | Baran et al. |
| 4,613,610 A | | 9/1986 | Wareing |
| 4,678,783 A | * | 7/1987 | Hidaka et al. .............. 514/218 |
| 4,686,237 A | | 8/1987 | Anderson |
| 4,739,073 A | | 4/1988 | Kathawala |
| 4,912,107 A | | 3/1990 | Kleinschroth et al. |
| 4,965,200 A | | 10/1990 | Chen et al. |
| 5,030,447 A | | 7/1991 | Joshi et al. |
| 5,084,482 A | | 1/1992 | Hirsch et al. |
| 5,116,870 A | | 5/1992 | Smith et al. |
| 5,135,935 A | | 8/1992 | Alberts et al. |
| 5,180,589 A | | 1/1993 | Joshi et al. |
| 5,273,995 A | | 12/1993 | Roth |
| 5,298,497 A | | 3/1994 | Tschollar et al. |
| 5,354,772 A | | 10/1994 | Kathawala |
| 5,470,832 A | | 11/1995 | Gibbs et al. |
| 5,475,029 A | | 12/1995 | Bradfute et al. |
| 5,514,696 A | | 5/1996 | Murugesan et al. |
| 5,519,035 A | * | 5/1996 | Maieses et al. .............. 514/309 |
| 5,530,001 A | | 6/1996 | Nakajima et al. |
| 5,591,772 A | | 1/1997 | Lane et al. |
| 5,602,098 A | | 2/1997 | Sebti et al. |
| 5,612,359 A | | 3/1997 | Murugesan |
| 5,622,985 A | | 4/1997 | Olukotun et al. |
| 5,723,456 A | | 3/1998 | Jirousek et al. |
| 5,756,453 A | | 5/1998 | Vedder et al. |
| 5,767,160 A | * | 6/1998 | Kaesemeyer ................. 514/565 |
| 5,830,910 A | * | 11/1998 | Mattson ...................... 514/411 |

FOREIGN PATENT DOCUMENTS

| | | |
|---|---|---|
| EP | 0 671 171 A1 | 9/1995 |
| JP | 09183797 A | 7/1997 |
| WO | WO 98/34626 | 8/1998 |

OTHER PUBLICATIONS

English Translation of Laufs, U., et al., "Neue Erkenntnisse über die Wirkung von HMG–CoA–Reduktase–Hemmern" Dtsch. Med. Wschr. 122:1255–1259 (1997).

O'Driscoll et al., "The HMG–CoA Reductase Inhibitor, Simvastatin, Improves Endothelial Function Within One Month," Circulation, vol. 94, No. 8, 1996, pp. 1–401.

Enders et al., "Stroke Protection by 3–hydroxy–3–methylglutaryl (HMG)–CoA Reductase Inhibitors Mediated by Endothelia Nitric Oxide Synthase," Proc. Natl. Acad. Sci. USA, vol. 95, Jul. 1998, pp. 8880–8885.

Endres et al., "Simvastatin Pretreatment Protects from Focal Cerebral Ischemia," Stroke, vol. 29, No. 1, Jan. 1998, p. 325.

Di Napoli et al., "Simvastatin Exerts a Direct Anti–Ischemic Effect: Evidence of a Nitric–Oxide Mediated Cardioprotection," Eur. Heart J., vol. 19, Aug. 1998, p. 124.

Laufs et al., "Inhibition of 3–hydroxy–3–methylglutaryl (HMG)–CoA Reductase Blocks Hypoxia–Mediated Down–Regulation of Endothelial Nitric Oxide Synthase," J. Biol. Chem., vol. 272, No. 50, Dec. 12, 1997, pp. 31725–31729.

PCT International Search Report (1999).

(List continued on next page.)

Primary Examiner—Frederick Krass
(74) Attorney, Agent, or Firm—Wolf, Greenfield & Sacks, P.C.

(57) ABSTRACT

A use for agents that disrupt actin cytoskeletal organization is provided. In the instant invention, agents that disrupt actin cytoskeletal organization are found to upregulate endothelial cell Nitric Oxide Synthase activity. As a result, agents that disrupt actin cytoskeletal organization are useful in treating or preventing conditions that result from the abnormally low expression and/or activity of endothelial cell Nitric Oxide Synthase. Such conditions include pulmonary hypertension, ischemic stroke, impotence, heart failure, hypoxia-induced conditions, insulin deficiency, progressive renal disease, gastric or esophageal motility syndrome, etc. Subjects thought to benefit mostly from such treatments include nonhyperlipidemics and nonhypercholesterolemics, but not necessarily exclude hyperlipidemics and hypercholesterolemics.

9 Claims, 6 Drawing Sheets

OTHER PUBLICATIONS

Blauw, G.J., "Stroke, Statins, and Cholesterol: A Meta–Analysis of Randomized, Placebo–Controlled, Double–Blind Trials With HMG–CoA Reductase Inhibitors," Stroke 28(5):946–950 (1997).

Boston Globe "Statins Found to Cut Risk of Stroke: Cholesterol Drugs Curbed Death Rate" (Jul. 23, 1997).

Bult, H., "Nitric Oxide and Atherosclerosis: Possible Implications for Therapy" Mol. Med. Today 2(12):510–518 (1996), Abstract.

Byington, R.P., et al., "Reduction in Cardiovascular Events During Pravastatin Therapy: Pooled Analysis of Clinical Events of the Pravastain Atherosclerosis Intervention Program" Circulation 92(9):2419–2425 (1995).

Casino, P.R., et al., "The Role of Nitric Oxide in Endothelium–Dependent Vasodilation of Hypercholesterolemic Patients" Circulation 88(6):2541–2547 (1993), Abstract.

Cooke, J.P., et al., "Nitric Oxide Synthase: Role in the Genesis of Vascular Disease" Annu. Rev. Med. 48:489–509 (1997), Abstract.

Crouse, J.R., et al., "Reductase Inhibitor Monotherapy and Stroke Prevention" Arch. Intern. Med. 157:1305–1310 (1997).

Dusting, G.J., "Nitric Oxide in Coronary Artery Disease: Roles in Atherosclerosis, Myocardial Reperfusion and Heart Failure" EXS 76:33–55 (1996), Abstract.

Giaid, A., et al., "Reduced Expression of Endothelial Nitric Oxide Synthase in the Lungs of Patients with Pulmonary Hypertension" New Eng. J. Med. 333(4):214–221 (1995).

Hebert, P.R., et al., "Cholesterol–Lowering Reduces Risks of Stroke and Total Mortality" Circulation 94 Suppl 1:I–744 (1996) Abstract 4351.

Hebert, P.R., et al., "Cholesterol Lowering and the Risk of Stroke" Arch. Intern. Med. 156:214–215 (1996).

Hislop, A., et al., "Endothelial Nitric Oxide Synthase in Hypoxic Newborn Porcine Pulmonary Vessels" Arch Dis Child Fetal Neonatal Ed., 77(1):F16–22 (Jul. 1997), Abstract.

Jessup, W., "Oxidized Lipoproteins and Nitric Oxide" Curr. Opin. Lipidol. 7(5):274–280 (1996), Abstract.

Laufs, U., et al., "Neue Erkenntnisse über die Wirkung von HMG–CoA–Reduktase–Hemmern" Dtsch. Med. Wschr. 122:1255–1259 (1997).

Macdonald, P., et al., "The Role of Nitric Oxide in Heart Failure Potential for Pharmacological Intervention" Drugs Aging 8(6):452–458 (1996), Abstract.

Martinez–Riera, A., et al., "Primary Prevention of Stroke" New Engl. J. Med. 334(17):1138–1139 (1996).

Massoudy, P. et al., "Cardioprotection by Cyclosporine A in Experimental Ischemia and Reperfusion—Evidence for a Nitric Oxide–Dependent Mechanism Mediated by Endothelin" Mol. Cell Cardio. 29, 535–544 (1997).

Munzel, T., et al., "The Physiology and Pathophysiology of the Nitric Oxide/Superoxide System" Herz 22(3):158–172 (1997), Abstract.

O'Driscoll, G., et al., "Simvastatin, an HMG–Coenzyme A Reductase Inhibitor, Improves Endothelial Function within 1 Month" Circulation 95(5):1126–1131 (1997), Abstract.

Rector, T.S., et al., "Randomized, Double–Blind, Placebo–Controlled Study of Supplemental Oral L–Arginine in Patients with Heart Failure" Circulation 93(2):2135–2141 (1996), Abstract.

Sacks, F.M., et al., "The Effect of Pravastatin on Coronary Events After Myocardial Infarction in Patients with Average Cholesterol Levels" New Engl. J. Med. 335(14):1001–1009 (1996)verage Cholesterol Levels.

Samdani, A.F., et al., "Nitric Oxide Synthase in Models of Focal Ischemia"Stroke 28(6):1283–1288 (1997), Abstract.

Sartor, G., et al., "Simvastatin Treatment of Hypercholesterolemia in Patients with Insulin Dependent Diabetes Mellitus" Int. J. Clin. Pharmacol. Ther. 33(1):3–6 (1995), Abstract.

Stroes, E., et al., "Tetrahydrobiopterin Restores Endothelial Function in Hypercholesterolemia" J. Clin. Invest. 99(1):41–46 (1997), Abstract.

Warshafsky, S., et al., "Efficacy of HMG–CoA Reductase Inhibitors For Prevention of Stroke "Abstract (1997).

Wolf, A., et al., "Dietary L–Arginine Supplementation Normalizes Platelet Aggregation in Hypercholesterolemic Humans" J. Am. Coll. Cardiol. 29(3):479–485 (1997), Abstract.

Yokoyama, M., et al., "Regulation of Nitric Oxide Synthase Gene Expression by Cytokines" J. Card. Fail. 2(4 Suppl):S179–S185 (1996), Abstract.

* cited by examiner

SEQUENCE LISTING

```
<160> NUMBER OF SEQ ID NOS: 4

<210> SEQ ID NO 1
<211> LENGTH: 25
<212> TYPE: DNA
<213> ORGANISM: Mus Musculus

<400> SEQUENCE: 1
gggctccctc cttccggctg ccacc                                       25

<210> SEQ ID NO 2
<211> LENGTH: 24
<212> TYPE: DNA
<213> ORGANISM: Mus Musculus

<400> SEQUENCE: 2
ggatccctgg aaaaggcggt gagg                                        24

<210> SEQ ID NO 3
<211> LENGTH: 20
<212> TYPE: DNA
<213> ORGANISM: Mus Musculus
```

```
<400> SEQUENCE: 3
accacagtcc atgccatcac                                               20

<210> SEQ ID NO 4
<211> LENGTH: 20
<212> TYPE: DNA
<213> ORGANISM: Mus Musculus

<400> SEQUENCE: 4
tccaccaccc tgttgctgta                                               20
```

UPREGULATION OF TYPE III ENDOTHELIAL CELL NITRIC OXIDE SYNTHASE BY AGENTS THAT DISRUPT ACTIN CYTOSKELETAL ORGANIZATION

GOVERNMENT SUPPORT

The work resulting in this invention was supported in part by NIH Grant No. RO1-HL-52233. The U.S. Government may be entitled to certain rights in the invention.

FIELD OF THE INVENTION

This invention relates to the use of agents that disrupt actin cytoskeletal organization as upregulators of Type III endothelial cell Nitric Oxide Synthase. Further, this invention relates to methods that employ agents that disrupt actin cytoskeletal organization to treat conditions that result from the abnormally low expression and/or activity of endothelial cell Nitric Oxide Synthase in a subject.

BACKGROUND OF THE INVENTION

Nitric oxide (NO) has been recognized as an unusual messenger molecule with many physiologic roles, in the cardiovascular, neurologic and immune systems (Griffith, T M et al., *J Am Coll Cardiol*, 1988, 12:797–806). It mediates blood vessel relaxation, neurotransmission and pathogen suppression. NO is produced from the guanidino nitrogen of L-arginine by NO Synthase (Moncada, S and Higgs, E A, *Eur J Clin Invest*, 1991, 21(4):361–374). In mammals, at least three isoenzymes of NO Synthase have been identified. Two, expressed in neurons (nNOS) and endothelial cells (Type III-ecNOS), are calcium-dependent, whereas the third is calcium-independent and is expressed by macrophages and other cells after induction with cytokines (Type II-iNOS) (Bredt, D S and Snyder, S H, *Proc Natl Acad Sci USA*, 1990, 87:682–685, Janssens, S P et al., *J Biol Chem*, 1992, 267:22964, Lyons, C R et al., *J Biol Chem*, 1992, 267:6370–6374). The various physiological and pathological effects of NO can be explained by its reactivity and different routes of formation and metabolism.

Recent studies suggest that a loss of endothelial-derived NO activity may contribute to the atherogenic process (O'Driscoll, G, et al., *Circulation*, 1997, 95:1126–1131). For example, endothelial-derived NO inhibits several components of the atherogenic process including monocyte adhesion to the endothelial surface (Tsao, P S et al., *Circulation*, 1994, 89:2176–2182), platelet aggregation (Radomski, M W, et al., *Proc Natl Acad Sci USA*, 1990, 87:5193–5197), vascular smooth muscle cell proliferation (Garg, U C and Hassid, A, *J Clin Invest*, 1989, 83:1774–1777), and vasoconstriction (Tanner, F C et al., *Circulation*, 1991, 83:2012–2020). In addition, NO can prevent oxidative modification of low-density lipoprotein (LDL) which is a major contributor to atherosclerosis, particularly in its oxidized form (Cox, D A and Cohen, M L, *Pharm Rev*, 1996, 48:3–19).

It has been shown in the prior art that hypoxia downregulates ecNOS expression and/or activity via decreases in both ecNOS gene transcription and mRNA stability (Liao, J K et al., *J Clin Invest*, 1995, 96:2661–2666, Shaul, P W et al., *Am J Physiol*, 1997, 272: L1005–L1012). Thus, ischemia-induced hypoxia may produce deleterious effects, in part, through decreases in ecNOS activity.

HMG-CoA (3-hydroxy-3-methylglutaryl-coenzyme A) reductase is the microsomal enzyme that catalyzes the rate limiting reaction in cholesterol biosynthesis (HMG-CoA6Mevalonate). An HMG-CoA reductase inhibitor inhibits HMG-CoA reductase, and as a result inhibits the synthesis of cholesterol. A number of HMG-CoA reductase inhibitors has been used to treat individuals with hypercholesterolemia. Clinical trials with such compounds have shown great reductions of cholesterol levels in hypercholesterolemic patients. Moreover, it has been shown that a reduction in serum cholesterol levels is correlated with improved endothelium-dependent relaxations in atherosclerotic vessels (Treasure, C B et al., *N Engl J Med*, 1995, 332:481–487). Indeed, one of the earliest recognizable benefits after treatment with HMG-CoA reductase inhibitors is the restoration of endothelium-dependent relaxations or ecNOS activity (supra, Anderson, T J et al., *N Engl J Med*, 1995, 332:488–493).

Although the mechanism by which HMG-CoA reductase inhibitors restore endothelial function is primarily attributed to the inhibition of hepatic HMG-CoA reductase and the subsequent lowering of serum cholesterol levels, little is known on whether inhibition of endothelial HMG-CoA reductase has additional beneficial effects on endothelial function.

By inhibiting L-mevalonate synthesis, HMG-CoA reductase inhibitors also prevent the synthesis of other important isoprenoid intermediates of the cholesterol biosynthetic pathway, such as farnesylpyrophosphate (FPP) and geranylgeranylpyrophosphate (GGPP) (Goldstein, J L and Brown, M S, *Nature*, 1990, 343:425–430). The isoprenoids are important lipid attachments for the post-translational modification of variety of proteins, including G-protein and G-protein subunits, Heme-a, nuclear lamins, Ras, and Ras-like proteins, such as Rho, Rab, Rac, Ral or Rap (Goldstein, J L and Brown, M S, supra; Casey, P J, *Science*, 1995, 268:221–225). The role that isoprenoids play in regulating ecNOS expression, however, is not known.

Pulmonary hypertension is a major cause of morbidity and mortality in individuals exposed to hypoxic conditions (Scherrer, U et al., *N Engl J Med*, 1996, 334:624–629). Recent studies demonstrate that pulmonary arterial vessels from patients with pulmonary hypertension have impaired release of NO (Giaid, A and Saleh, D, *N Engl J Med*, 1995, 333:214–221, Shaul, P W, *Am J Physiol*, 1997, 272: L1005–L1012). Additionally, individuals with pulmonary hypertension demonstrate reduced levels of ecNOS expression in their pulmonary vessels and benefit clinically from inhalation nitric oxide therapy (Roberts, J D et al., *N Engl J Med*, 1997, 336:605–610, Kouyoumdjian, C et al., *J Clin Invest*, 1994, 94:578–584). Conversely, mutant mice lacking ecNOS gene or newborn lambs treated with the ecNOS inhibitor, Nw-monomethyl-L-arginine (LNMA), develop progressive elevation of pulmonary arterial pressures and resistance (Steudel, W et al., *Circ Res*, 1997, 81:34–41, Fineman, J R et al., *J Clin Invest*, 1994, 93:2675–2683). It has also been shown in the prior art that hypoxia causes pulmonary vasoconstriction via inhibition of endothelial cell nitric oxide synthase (ecNOS) expression and activity (Adnot, S et al., *J Clin Invest*, 1991, 87:155–162, Liao, J K et al., *J Clin Invest*, 1995, 96, 2661–2666). Hence, hypoxia-mediated downregulation of ecNOS may lead to the vasoconstrictive and structural changes associated with pulmonary hypertension.

Often cited as the third most frequent cause of death in the developed countries, stroke has been defined as the abrupt impairment of brain function caused by a variety of pathologic changes involving one or several intracranial or extracranial blood vessels. Approximately 80% of all strokes are ischemic strokes, resulting from restricted blood flow.

Mutant mice lacking the gene for ecNOS are hypertensive (Huang, P L et al., *Nature*, 1995, 377:239–242, Steudel, W et al., *Circ Res*, 1997, 81:34–41) and develop greater intimal smooth muscle proliferation in response to cuff injury. Furthermore, occlusion of the middle cerebral artery results in 21% greater infarct size in "ecNOS knockout" mice compared to wildtype mice (Huang, Z et al., *J Cereb Blood Flow Metab*, 1996, 16:981–987). These findings suggest that the ecNOS production may play a role in cerebral infarct formation and sizes. Additionally, since most patients with ischemic strokes have average or normal cholesterol levels, little is known on what the potential benefits of HMG-CoA reductase inhibitor administration would be in cerebrovascular events.

There exists a need to identify agents that improve endothelial cell function.

There also exists a need to identify agents that can be used acutely or in a prophylactic manner to treat conditions that result from low levels of endothelial cell Nitric Oxide Synthase.

SUMMARY OF THE INVENTION

The invention involves the discovery that agents which disrupt actin cytoskeletal organization can upregulate endothelial cell Nitric Oxide Synthase (Type III) expression. The invention, therefore, is useful whenever it is desirable to restore endothelial cell Nitric Oxide Synthase activity or increase such activity in a cell, tissue or subject, provided the cell or the tissue expresses endothelial cell Nitric Oxide Synthase.

Nitric Oxide Synthase activity is involved in many conditions, including impotence, heart failure, gastric and esophageal motility disorders, kidney disorders such as kidney hypertension and progressive renal disease, insulin deficiency, etc. Individuals with such conditions would benefit from increased endothelial cell Nitric Oxide Synthase activity. It also was known that individuals with pulmonary hypertension demonstrate reduced levels of Nitric Oxide Synthase expression in their pulmonary vessels and benefit clinically from inhalation of Nitric Oxide. The invention therefore is particularly useful for treating pulmonary hypertension. It also has been demonstrated that hypoxia causes an inhibition of endothelial cell Nitric Oxide Synthase activity. The invention therefore is useful for treating subjects with hypoxia-induced conditions. It also has been discovered, surprisingly, that agents which disrupt actin cytoskeletal organization are useful for reducing brain injury that occurs following a stroke.

According to one aspect of the invention, a method is provided for increasing endothelial cell Nitric Oxide Synthase activity in a subject who would benefit from increased endothelial cell Nitric Oxide Synthase activity in a tissue. The method involves administering to a subject in need of such treatment an agent that disrupts actin cytoskeletal organization in an amount(s) effective to increase endothelial cell Nitric Oxide Synthase activity in the tissue of the subject, provided that the agent that disrupts actin cytoskeletal organization is not a rho GTPase function inhibitor. In one important embodiment agents that disrupt actin cytoskeletal organization do not affect cholesterol levels in a subject. In certain embodiments, however, agents that disrupt actin cytoskeletal organization as well as increasing endothelial cell Nitric Oxide Synthase activity in the tissue of a subject can also affect cholesterol levels in the subject. In certain embodiments, the subject is nonhyperlipidimic. In other embodiments the amount is sufficient to increase endothelial cell Nitric Oxide Synthase activity above normal baseline levels established by age-controlled groups, described in greater detail below.

The subject can have a condition characterized by an abnormally low level of endothelial cell Nitric Oxide Synthase activity which is hypoxia-induced. In other embodiments the subject can have a condition comprising an abnormally low level of endothelial cell Nitric Oxide Synthase activity which is chemically induced. In still other embodiments the subject can have a condition comprising an abnormally low level of endothelial cell Nitric Oxide Synthase activity which is cytokine induced. In certain important embodiments, the subject has pulmonary hypertension or an abnormally elevated risk of pulmonary hypertension. In other important embodiments, the subject has experienced an ischemic stroke or has an abnormally elevated risk of an ischemic stroke. In still other important embodiments, the subject has heart failure or progressive renal disease. In yet other important embodiments, the subject is chronically exposed to hypoxic conditions.

According to any of the foregoing embodiments, the preferred agent that disrupts actin cytoskeletal organization is selected from the group consisting of a myosin light chain kinase inhibitor, a myosin light chain phosphatase, a protein kinase N inhibitor, a phospatidylinositol 4-phosphate 5-kinase inhibitor, and cytochalasin D. In some embodiments the myosin light chain kinase inhibitor is selected from the group consisting of 2,3-butanedione 2-monoxime, 1-(5-iodonaphthalene-1-sulphonyl)-1-hexahydro-1,4-diazepine hydrochloride, and 1-(5-isoquinolinesulphonyl)-2-methylpiperazine dihydro-chloride. Likewise, in any of the foregoing embodiments, the method can further comprise co-administering an endothelial cell Nitric Oxide Synthase substrate and/or co-administering an agent other than an agent that disrupts actin cytoskeletal organization that also increases endothelial cell Nitric Oxide Synthase activity, and/or co-administering at least one different agent that disrupts actin cytoskeletal organization. A preferred agent other than an agent that disrupts actin cytoskeletal organization is selected from the group consisting of estrogens and angiotensin-converting enzyme (ACE) inhibitors. The agents may be administered to a subject who has a condition or prophylactically to a subject who has a risk, and more preferably, an abnormally elevated risk, of developing a condition. The inhibitors also may be administered acutely.

According to another aspect of the invention, a method is provided for increasing endothelial cell Nitric Oxide Synthase activity in a subject to treat a condition favorably affected by an increase in endothelial cell Nitric Oxide Synthase activity in a tissue. Such conditions are exemplified above. The method involves administering to a subject in need of such treatment an agent that disrupts actin cytoskeletal organization in an amount effective to increase endothelial cell Nitric Oxide Synthase activity in the tissue of the subject, provided that the agent that disrupts actin cytoskeletal organization is not a rho GTPase function inhibitor. In important embodiments, agents that disrupt actin cytoskeletal organization do not affect cholesterol levels in a subject. In certain embodiments, however, agents that disrupt actin cytoskeletal organization as well as increase endothelial cell Nitric Oxide Synthase activity in the tissue of a subject can also affect cholesterol levels in the subject. In certain embodiments, the subject is nonhyperlipidimic. Important conditions are as described above. Also as described above, the method can involve co-administration of substrates of endothelial cell Nitric Oxide Synthase and/or co-administering an agent other than an agent that disrupts actin cytoskeletal organization that also increases endothelial cell Nitric Oxide Synthase activity, and/or co-administering at least one different agent that disrupts actin cytoskeletal organization. Preferred compounds are as described above. As above, the agents that disrupt actin cytoskeletal organization with or without the co-administered compounds can be administered, inter alia, acutely or prophylactically.

According to another aspect of the invention, a method is provided for reducing brain injury resulting from stroke. The method involves administering to a subject having an abnormally high risk of an ischemic stroke an agent that disrupts actin cytoskeletal organization in an amount effective to increase endothelial cell Nitric Oxide Synthase activity in the brain of the subject, provided that the agent that disrupts actin cytoskeletal organization is not a rho GTPase function inhibitor. As above, important embodiments include the agent being selected from the group consisting of a myosin light chain kinase inhibitor, a myosin light chain phosphatase, a protein kinase N inhibitor, a phospatidylinositol 4-phosphate 5-kinase inhibitor, and cytochalasin D. As above, in some embodiments a myosin light chain kinase inhibitor is selected from the group consisting of 2,3-butanedione 2-monoxime, 1-(5-iodonaphthalene-1-sulphonyl)-1H-hexahydro-1,4-diazepine hydrochloride, and 1-(5-isoquinolinesulphonyl)-2-methylpiperazine dihydrochloride. Also as above, important embodiments include co-administering a substrate of endothelial cell Nitric Oxide Synthase and/or co-administering an agent other than an agent that disrupts actin cytoskeletal organization that also increases endothelial cell Nitric Oxide Synthase activity, and/or co-administering at least one different agent that disrupts actin cytoskeletal organization. Likewise, important embodiments include prophylactic and acute administration of the agent(s).

According to another aspect of the invention, a method is provided for treating pulmonary hypertension. The method involves administering to a subject in need of such treatment an agent that disrupts actin cytoskeletal organization in an amount effective to increase pulmonary endothelial cell Nitric Oxide Synthase activity in the subject, provided that the agent that disrupts actin cytoskeletal organization is not a rho GTPase function inhibitor. Particularly important embodiments are as described above in connection with the methods for treating brain injury. Another important embodiment is administering the agent prophylactically to a subject who has an abnormally elevated risk of developing pulmonary hypertension, including subjects that are chronically exposed to hypoxic conditions.

According to another aspect of the invention, a method for treating heart failure is provided. The method involves administering to a subject in need of such treatment an agent that disrupts actin cytoskeletal organization in an amount effective to increase vascular endothelial cell Nitric Oxide Synthase activity in the subject, provided that the agent that disrupts actin cytoskeletal organization is not a rho GTPase function inhibitor. As discussed above, important embodiments include prophylactic and acute administration of the agent(s). Preferred compounds and co-administration schemes are as described above.

According to yet another aspect of the invention, a method is provided for treating progressive renal disease. The method involves administering to a subject in need of such treatment an agent that disrupts actin cytoskeletal organization in an amount effective to increase renal endothelial cell Nitric Oxide Synthase activity in the kidney of the subject, provided that the agent that disrupts actin cytoskeletal organization is not a rho GTPase function inhibitor. Important embodiments and preferred compounds and schemes of co-administration are as described above in connection with heart failure.

According to another aspect of the invention, a method for increasing blood flow in a tissue of a subject is provided. The method involves administering to a subject in need of such treatment a first agent that disrupts actin cytoskeletal organization in an amount effective to increase endothelial cell Nitric Oxide Synthase activity in the tissue of the subject, provided that the first agent is not an agent selected from the group consisting of a rho GTPase function inhibitor and fasudil. In certain embodiments the first agent is not a myosin light chain kinase inhibitor. In other embodiments the first agent is selected from the group consisting of a myosin light chain phosphatase, a protein kinase N inhibitor, a phospatidylinositol 4-phosphate 5-kinase inhibitor, and cytochalasin D. Other important embodiments include co-administering a second agent to the subject with a condition treatable by the second agent in an amount effective to treat the condition, whereby the delivery of the second agent to a tissue of the subject is enhanced as a result of the increased blood flow. In certain embodiments where a second agent is administered, the condition treatable by the second agent does not involve the brain tissue.

The invention also involves the use of agents that disrupt actin cytoskeletal organization in the manufacture of medicaments for treating the above-noted conditions. Important conditions, compounds, etc. are as described above. The invention further involves pharmaceutical preparations that are cocktails of agents that disrupt actin cytoskeletal organization according to the invention [non-rho GTPase function inhibitor(s)]. In certain embodiments, however, the cocktails can include a rho GTPase function inhibitor(s) that disrupts actin cytoskeletal organization together with the non-rho GTPase function inhibitor agent of the invention. The invention also involves pharmaceutical preparations that are cocktails of agents that disrupt actin cytoskeletal organization together with agents other than agents that disrupt actin cytoskeletal organization that also increase ecNOS activity in a cell.

The invention also involves methods for increasing ecNOS activity in a cell by contacting the cell with an effective amount of an agent that disrupts actin cytoskeletal organization (excluding rho GTPase function inhibitors), alone, or together with any of the agents co-administered as described above, or as a cocktail as described above.

In any of the foregoing aspects of the invention the agent can be a non-fasudil agent that disrupts actin cytoskeletal organization.

These and other aspects of the invention are described in greater detail below.

DETAILED DESCRIPTION OF THE INVENTION

Figure 1A:
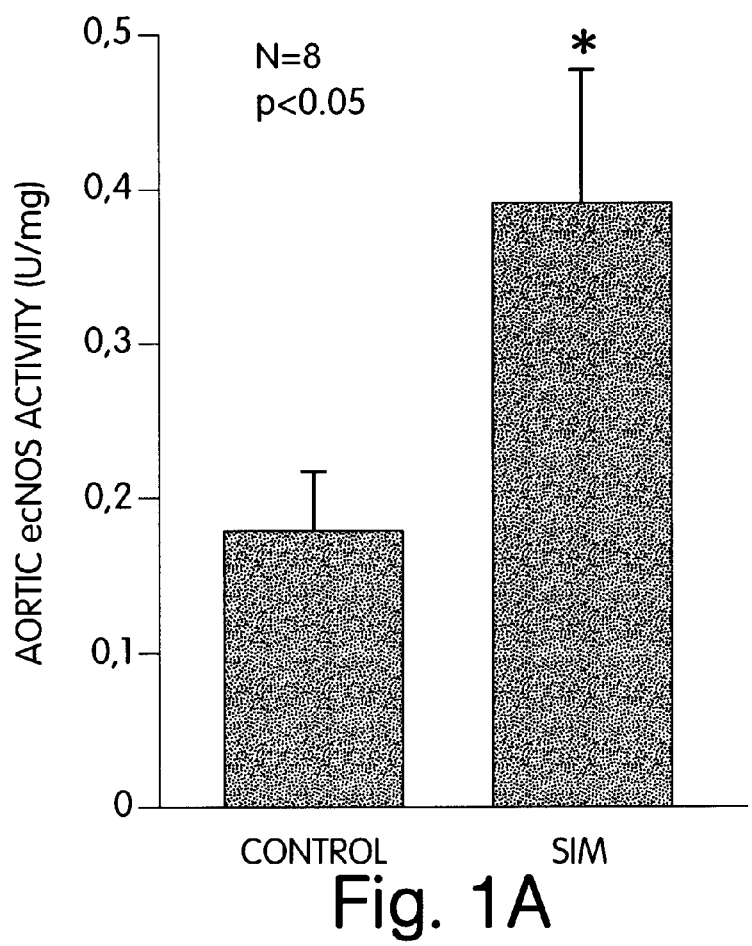
FIG. 1. ecNOS activity (FIG. 1A) and expression in wild-type SV-129 mice aortas (FIG. 1B) with and without treatment with simvastatin for 14 days.

The invention is useful whenever it is desirable to increase endothelial cell Nitric Oxide Synthase (Type III isoform) activity in a cell, in a tissue, or in a subject. A subject as used herein includes humans, non human primates, dogs, cats, sheep, goats, cows, pigs, horses and rodents. The invention thus is useful for therapeutic purposes and also is useful for research purposes such as in testing in animal or in vitro models of medical, physiological or metabolic pathways or conditions. Nitric Oxide Synthase is the enzyme that catalyzes the reaction that produces nitric oxide from the substrate L-arginine. As the name implies, endothelial cell nitric oxide Synthase refers to the Type III isoform of the enzyme found in the endothelium.

By "ecNOS activity", it is meant the ability of a cell to generate nitric oxide from the substrate L-arginine. Increased ecNOS activity can be accomplished in a number of different ways. For example, an increase in the amount of ecNOS protein or an increase in the activity of the protein (while maintaining a constant level of the protein) can result in increased "activity". An increase in the amount of protein available can result from increased transcription of the ecNOS gene, increased stability of the ecNOS mRNA or a decrease in ecNOS protein degradation. (The term "expression" is used interchangeably with the term "activity" throughout this application).

The ecNOS activity in a cell or in a tissue can be measured in a variety of different ways. A direct measure would be to measure the amount of ecNOS present. Another direct measure would be to measure the amount of conversion of arginine to citrulline by ecNOS or the amount of generation of nitric oxide by ecNOS under particular conditions, such as the physiologic conditions of the tissue. The ecNOS activity also can be measured more indirectly, for example by measuring mRNA half-life (an upstream indicator) or by a phenotypic response to the presence of nitric oxide (a downstream indicator). One phenotypic measurement employed in the art is detecting endothelial dependent relaxation in response to a acetylcholine, which response is affected by ecNOS activity. The level of nitric oxide present in a sample can be measured using a nitric oxide meter. All of the foregoing techniques are well known to those of ordinary skill in the art, and some are described in the examples below.

The present invention, by causing an increase in ecNOS activity, permits not only the re-establishment of normal base-line levels of ecNOS activity, but also allows increasing such activity above normal base-line levels. Normal base-line levels are the amounts of activity in a normal control group, controlled for age and having no symptoms which would indicate alteration of endothelial cell Nitric Oxide Synthase activity (such as hypoxic conditions, hyperlipidemia and the like). The actual level then will depend upon the particular age group selected and the particular measure employed to assay activity. Specific examples of various measures are provided below. In abnormal circumstances, e.g. hypoxic conditions, pulmonary hypertension, etc., endothelial cell Nitric Oxide Synthase activity is depressed below normal levels. Surprisingly, when using agents that disrupt actin cytoskeletal organization according to the invention, not only can normal base-line levels be restored in such abnormal conditions, but endothelial cell Nitric Oxide Synthase activity can be increased desirably far above normal base-line levels of endothelial cell Nitric Oxide Synthase activity. Thus, "increasing activity" means any increase in endothelial cell Nitric Oxide Synthase activity in the subject resulting from the treatment with agents that disrupt actin cytoskeletal organization according to the invention, including, but not limited to, such activity as would be sufficient to restore normal base-line levels and such activity as would be sufficient to elevate the activity above normal base-line levels.

As mentioned above, Nitric Oxide Synthase activity is involved in many conditions, including stroke, pulmonary hypertension, impotence, heart failure, gastric and esophageal motility disorders, kidney disorders such as kidney hypertension and progressive renal disease, insulin deficiency, hypoxia-induced conditions, etc. In one embodiment of the invention the decrease in endothelial cell Nitric Oxide Synthase activity is cytokine induced. Cytokines are soluble polypeptides produced by a wide variety of cells that control gene activation and cell surface molecule expression. They play an essential role in the development of the immune system and thus in the development of an immune response. However, besides their numerous beneficial properties, they have also been implicated in the mechanisms for the development of a variety of inflammatory diseases. For example, the cytokines TNF-a and IL-1 are thought to be part of the disease causing mechanism of non-cholesterol induced atherosclerosis, transplant arterial sclerosis, rheumatoid arthritis, lupus, scleroderma, emphysema, etc. Subjects of such disorders exhibit lower levels of endothelial cell Nitric Oxide Synthase activity (which is thus "cytokine induced"), and may benefit from therapy using the agents of the instant invention.

One important embodiment of the invention is treatment of ischemic stroke. Ischemic stroke (ischemic cerebral infarction) is an acute neurologic injury that results from a decrease in the blood flow involving the blood vessels of the brain. Ischemic stroke is divided into two broad categories, thrombotic and embolic.

A surprising finding was made in connection with the treatment of ischemic stroke. In particular, it was discovered that treatment according to the invention can reduce the brain injury that follows an ischemic stroke. Brain injury reduction, as demonstrated in the examples below, can be measured by determining a reduction in infarct size in the treated versus the control groups. Likewise, functional tests measuring neurological deficits provided further evidence of reduction in brain injury in the treated animals versus the controls. Cerebral blood flow also was better in the treated animals versus the controls. Thus, in the various accepted models of brain injury following stroke, a positive effect was observed in the treated animals versus the control animals. It is believed that all of the foregoing positive results are attributable to the upregulation of endothelial cell Nitric Oxide Synthase activity, which is believed demonstrated in the examples below.

An important embodiment of the invention is treatment of a subject with an abnormally elevated risk of an ischemic stroke. As used herein, subjects having an abnormally elevated risk of an ischemic stroke are a category determined according to conventional medical practice. This category includes, for example, subjects which are having elected vascular surgery. Typically, the risk factors associated with cardiac disease are the same as are associated with stroke. The primary risk factors include hypertension, hypercholesterolemia, and smoking. In addition, atrial fibrillation or recent myocardial infarction are important risk factors.

The treatment of stroke can be for patients who have experienced a stroke or can be a prophylactic treatment. If prophylactic, then the treatment is for subjects having an abnormally elevated risk of an ischemic stroke, as described above. If the subject has experienced a stroke, then the treatment can include acute treatment. Acute treatment means administration of the agents that disrupt actin cytoskeletal organization at the onset of symptoms of the condition or at the onset of a substantial change in the symptoms of an existing condition.

Another important embodiment of the invention is treatment of pulmonary hypertension. Pulmonary hypertension is a disease characterized by increased pulmonary arterial pressure and pulmonary vascular resistance. Hypoxemia, hypocapnia, and an abnormal diffusing capacity for carbon monoxide are almost invariable findings of the disease. Additionally, according to the present invention, patients with pulmonary hypertension also have reduced levels of ecNOS expression and/or activity in their pulmonary vessels. Traditionally, the criteria for subjects with, or at risk for pulmonary hypertension are defined on the basis of clinical and histological characteristics according to Heath and Edwards (*Circulation*, 1958, 18:533–547).

Subjects may be treated prophylactically to reduce the risk of pulmonary hypertension or subjects with pulmonary hypertension may be treated long term and/or acutely. If the treatment is prophylactic, then the subjects treated are those with an abnormally elevated risk of pulmonary hypertension. A subject with an abnormally elevated risk of pulmonary hypertension is a subject with chronic exposure to hypoxic conditions, a subject with sustained vasoconstriction, a subject with multiple pulmonary emboli, a subject with cardiomegaly and/or a subject with a family history of pulmonary hypertension.

Another important embodiment of the invention involves treating hypoxia-induced conditions. Hypoxia as used herein is defined as the decrease below normal levels of oxygen in a tissue. Hypoxia can result from a variety of circumstances, but most frequently results from impaired lung function. Impaired lung function can be caused by emphysema, cigarette smoking, chronic bronchitis, asthma, infectious agents, pneumonitis (infectious or chemical), lupus, rheumatoid arthritis, inherited disorders such as cystic fibrosis, obesity, $\alpha_1$-antitrypsin deficiency and the like. It also can result from non-lung impairments such as from living at very high altitudes. Hypoxia can result in pulmonary vasoconstriction via inhibition of ecNOS activity.

Another important embodiment of the invention is the treatment of heart failure. Heart failure is a clinical syndrome of diverse etiologies linked by the common denominator of impaired heart pumping and is characterized by the failure of the heart to pump blood commensurate with the requirements of the metabolizing tissues, or to do so only from an elevating filling pressure.

In certain aspects of the invention, agents that disrupt actin cytoskeletal organization are administered to subjects that would benefit from increased endothelial cell Nitric Oxide Synthase activity. The administration of one or more agents that disrupt actin cytoskeletal organization is in an amount(s) effective to increase endothelial cell Nitric Oxide Synthase activity in tissue of the subject, provided that the agent that disrupts actin cytoskeletal organization used is not a rho GTPase function inhibitor (See later discussion). In certain embodiments, the subject is both nonhypercholesterolemic and nonhypertriglyceridemic, i.e., nonhyperlipidemic. Such subjects are thought to benefit mostly from the treatments of the invention, but the treatments do not necessarily exclude hyperlipidemic and hypercholesterolemic subjects.

A nonhypercholesterolemic subject is one that does not fit the current criteria established for a hypercholesterolemic subject. A nonhypertriglyceridemic subject is one that does not fit the current criteria established for a hypertriglyceridemic subject (See, e.g., Harrison's Principles of Experimental Medicine, 13th Edition, McGraw-Hill, Inc., N.Y.). Hypercholesterolemic subjects and hypertriglyceridemic subjects are associated with increased incidence of premature coronary heart disease. A hypercholesterolemic subject has an LDL level of >160 mg/dL or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a hyperlipidemic subject is defined as one whose cholesterol and triglyceride levels equal or exceed the limits set as described above for both the hypercholesterolemic and hypertriglyceridemic subjects.

The invention involves treatment of the foregoing conditions using agents that disrupt actin cytoskeletal organization. Actin comprises a large proportion of the cytoplasmic proteins of many cells. Actin is present primarily in its globular form (G-actin), a single polypeptide 375 amino acids long, and is associated with one molecule of noncovalently bound ATP. The terminal phosphate of the ATP is hydrolysed after the actin polymerizes to form actin filaments (fibrous actin or F-actin). Actin filaments consist of a tight-helix of uniformly oriented actin monomers. They are polar structures, with two structurally different ends, and form the "core" of the actin cytoskeleton. An actin cytoskeleton is thus a three dimensional structure that results from the interaction between actin filaments and other molecules that associate with the actin filaments (e.g., cross-linking proteins such as filamin). The actin cytoskeleton mediates a variety of biological functions in all eukaryotic cells. In addition to providing a structural framework around which cell shape and polarity are defined, its dynamic properties provide the driving force for cells to move and to divide.

According to the present invention, it has been discovered that agents which disrupt actin cytoskeletal organization control endothelial cell Nitric Oxide Synthase activity. In particular, agents that disrupt actin cytoskeletal organization upregulate endothelial cell Nitric Oxide Synthase activity.

According to the present invention, "agents that disrupt actin cytoskeletal organization" are compounds, natural or synthetic, that interfere with actin cytoskeletal organization. Typically such agents will interfere, for example, with stress fiber formation (contractile bundles of actin filaments and myosin), and/or focal contact (or adhesion plaque) assembly and upregulate endothelial cell Nitric Oxide Synthase activity. The effects of such agents in a cell or in a tissue on actin cytoskeletal organization can be measured according to any art recognized method. For example, a direct measure would be to perform phalloidin staining (Sigma) on intact cells. A person of ordinary skill in the art could then determine (and quantitate) the effects of the agents of the invention by examining, for example, the structure of the stained actin stress-fibers and comparing such structure with the one which is normal and characteristic of an untreated cell.

Agents that disrupt actin cytoskeletal organization can exert their effects at different levels and thus comprise different categories of agents useful for practicing the present invention. The different categories include agents from those that disrupt actin cytoskeletal organization at the nucleic acid level to agents that disrupt actin cytoskeletal organization at the protein level.

Agents that disrupt actin cytoskeletal organization at the nucleotide level include chemicals, antisense nucleic acids, antibodies, catalytic nucleic acids including ribozymes, and proteins which interfere with the expression of a gene that encodes a polypeptide which is a component of the actin cytoskeleton. Such exemplary polypeptides include but are not limited to actin, myosin, tropomyosin, troponin, titin, nebulin, α-actinin, myomesin, C protein, filamin, talin, vinculin, capping protein, fibronectin receptor, ezrin, radixin, moiesin and the like.

Agents that disrupt actin cytoskeletal organization at the protein level include organic molecules that inhibit or alter the formation and organization of the actin cytoskeleton by interfering (e.g., via antibody binding, etc.) or altering (e.g., via post-translational modification) an individual component of the actin cytoskeleton. Specifically included are proteins, peptides and lipid derivatives. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

In certain embodiments, agents that disrupt actin cytoskeletal organization include myosin light chain kinase (MLCK-Ser/Thr kinases) inhibitors, myosin light chain phosphatase (MLCP) stimulators, protein kinase N (PKN) inhibitors, phospatidylinositol 4-phosphate 5-kinase (PIP5K) inhibitors, and cytochalasin D. Exemplary myosin light chain kinase inhibitors include BDM [2,3-butanedione 2-monoxime], ML-7 [1-(5-iodonaphthalene-1-sulphonyl)-1H-hexahydro-1,4-diazepine hydrochloride], ML-9 [1-(5-chloronaphthalene-1-sulfonyl)-1H-hexahydro-1,4-diazepine hydrochloride], wortmannin, H-7 [1-(5-isoquinoline sulphonyl)-2-methylpiperazine dihydrochloride], Fasudil (HA1077) [Hexahydro-1-(5-isoquinolinesulphonyl)-1H-1,4-diazepine], W-7 [N-(6-Aminohexyl)-5-chloro-1-naphthalenesulfonamide] and A-3 [N-(6-Aminoethyl)-5-chloro-1-naphthalenesulfonamide]. In preferred embodiments, agents that disrupt actin cytoskeletal organization include BDM, ML-7, H-7 and cytochalasin D. Exemplary PKN inhibitors include "dominant negative" PKN peptides and purine analogues such as 6-thioguanine. Exemplary PIP5K inhibitors include "dominant negative" PIP5K peptides. Exemplary MLCP stimulators include nucleic acids that encode functional MLCP proteins and peptides (i.e., maintain the phosphatase activity of MLCP) and that are overexpressed (via an expression vector) in the cells of interest of a subject according to the invention.using genetic approaches well known in the art.

Cytochalasin D is a preferred agent of the invention that belongs to the family of mold metabolites called cytochalasins. Cytochalasin D is thought to exert its function as an agent that disrupts actin cytoskeletal organization by affecting actin polymerization. Other members of the cytochalasin family share this property (e.g., Cytochalasin B), and are thus useful according to the invention.

Examples of agents that disrupt actin cytoskeletal organization also include "dominant negative" polypeptides of the polypeptide components of the actin cytoskeleton, some of which are exemplified above. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the application of or expression of a dominant negative polypeptide is a reduction in function of active proteins. One of ordinary skill in the art can assess the potential for a dominant negative variant of a protein, and using standard mutagenesis techniques to create one or more dominant negative variant polypeptides. For example, given the teachings contained herein and in the art, one of ordinary skill in the art can modify the sequence of a polypeptide (or the gene encoding a polypeptide) of an actin cytoskeletal component (as described earlier, e.g., actin, myosin, filamin, etc.) by site-specific mutagenesis, scanning mutagenesis, partial gene deletion or truncation, and the like. See, e.g., U.S. Pat. No. 5,580,723 and Sambrook et al., *Molecular Cloning. A Laboratory Manual*, Second Edition, Cold Spring Harbor Laboratory Press, 1989. The skilled artisan then can test the population of mutagenized polypeptides for diminution in a selected activity (e.g., impaired myosin light chain phosphorylation and upregulation of ecNOS activity) and/or for retention of such an activity. Other similar methods for creating and testing dominant negative variants of a protein will be apparent to one of ordinary skill in the art.

Other examples of agents that disrupt actin cytoskeletal organization include polypeptides which bind to components of the actin cytoskeleton and to complexes of the components of the actin cytoskeleton and binding partners. The invention, therefore, embraces peptide binding agents which, for example, can be antibodies or fragments of antibodies having the ability to selectively bind to components of the actin cytoskeleton. Antibodies include polyclonal and monoclonal antibodies, prepared according to conventional methodology.

A rho GTPase is a small, membrane-bound, Ras-related GTP-binding protein that functions by binding and hydrolyzing GTP. Rho GTPases function as molecular switches, cycling between an inactive GDP-bound conformation and an active GTP-bound conformation. According to the present invention, "rho GTPase function inhibitors" are compounds, natural or synthetic, that inhibit the normal function and localization of rho GTPases (i.e., impair GTP binding by rho GTPases) and upregulate endothelial cell Nitric Oxide Synthase activity. Such compounds can inhibit rho GTPase function at different levels and thus comprise different categories of agents useful for practicing the present invention. The different categories include agents from those that inhibit rho GTPases at the nucleic acid level to agents that inhibit rho GTPases at the protein level.

Agents that inhibit rho GTPases at the nucleotide level include chemicals, antisense nucleic acids, antibodies, catalytic nucleic acids including ribozymes, and proteins which repress expression of a rho GTPase gene locus.

Agents that inhibit rho GTPases at the protein level include organic molecules that alter the intrinsic GTPase activity of the rho GTP-binding protein, organic molecules that inhibit GDP/GTP exchange, and organic molecules that inhibit or alter post-translational modifications of rho GTPases. Specifically included are proteins, peptides and lipid derivatives.

Examples of agents that inhibit or reduce the intrinsic GTPase activity of a rho GTP-binding protein include cyclosporin, and "dominant negative" polypeptides of the rho GTPase. A dominant negative polypeptide is as described previously.

Dominant negative rho GTPase proteins include variants in which a portion of the GTP catalytic site has been mutated or deleted to reduce or eliminate GTP binding. Other examples include rho GTPase variants in which the conserved CAAX motif at their carboxy-terminus has been mutated or deleted to reduce or eliminate post-tranlational modification. (C, cysteine; A, aliphatic amino acid; X, any amino acid). One of ordinary skill in the art can readily prepare such modifications. Examples of dominant negative rho GTPase peptides are described in the Examples section and include N19RhoA and CAAXRhoA.

Other examples of agents that inhibit or reduce the intrinsic GTPase activity of a rho GTP-binding protein include polypeptides which bind to rho GTPase polypeptides and to complexes of rho GTPase polypeptides and binding partners. The invention, therefore, embraces peptide binding agents which, for example, can be antibodies or fragments of antibodies having the ability to selectively bind to rho GTPase polypeptides. Antibodies include polyclonal and monoclonal antibodies, prepared according to conventional methodology.

Examples of agents that inhibit the GDP/GTP exchange include proteins and peptides that inhibit GDP-dissociation such as Ly-GDI and RhoGDI-3. Preferably, using genetic approaches well known in the art, such proteins and peptides can be overexpressed (via an expression vector) in the cells of interest of a subject according to the invention.

Post-translational modifications of rho GTPases are important in that they are necessary for the proper attachment (and thus function) of the rho GTPases to the cell membrane. If rho GTPase polypeptides cannot be properly modified (or if they are overmodified), they accumulate in the cytosol and are rendered inactive. Examples of agents that inhibit post-translational modifications of rho GTPases include geranylgeranylation inhibitors and guanine nucleotide exchange inhibitors.

Geranylgeranylation inhibitors are compounds (natural or synthetic) that interfere with the geranylgeranylation of rho GTPases, and include proteins, peptides and lipid derivatives. Thus, geranylgeranylation inhibition of rho GTPases can occur either by preventing geranylgeranyl-pyrophosphate synthesis, or by inhibiting the enzyme geranylgeranyl transferase (GGT) which attaches geranylgeranyl-pyrophosphate to the CAAX motif of rho GTPases. Geranylgeranyl-pyrophosphate synthesis inhibition can be performed by preventing or inhibiting the formation of any of the intermediates in the geranylgeranyl-pyrophosphate synthesis pathway. Examples include mevalonate inhibitors, isopentenyl-pyrophosphate inhibitors, geranyl-pyrophosphate inhibitors, famesyl-pyrophosphate inhibitors and geranylgeranyl-pyrophosphate inhibitors. Examples of such compounds include famesyl-transferase inhibitors disclosed in U.S. Pats. Nos. 5,705,686 and 5,602,098, inhibitors of geranylgeranyl-transferase disclosed in U.S. Pat. No. 5,470,832, the disclosure of which is incorporated herein by reference, and a-hydroxyfarnesylphosphonic acid. Additional geranylgeranyl-transferase inhibitors include GGTI-298 (Finder, J D et al., *J Biol Chem*, 1997,272:13484–13488).

Guanine nucleotide exchange inhibitors are agents that also post-translationaly modify and inactivate rho GTPases. They include bacterial protein toxins that ADP-ribosylate or glucosylate rho GTPases, or compounds that inhibit rho GTPase-specific guanine nucleotide exchange factor (GEF). Preferred such agents according to the invention include *Clostridium botulinum* C3 transferase. The C3 transferase enzymatically catalyses the transfer of ADP from NADH to Asp-41 of rho, rendering the rho GTPase resistant to GTP/GDP exchange by the rho GTPase-specific guanine nucleotide exchange factors (GEFs). (See the Examples section also). The C3 transferase is administered in protein form, or more preferably, its cDNA is expressed using an expression vector in the cells of interest of a subject according to the invention. Rho GTPase-specific guanine nucleotide exchange factor inhibitors include chemicals, antisense nucleic acids, antibodies, catalytic nucleic acids including ribozymes, proteins which repress expression of a rho GTPase-specific guanine nucleotide exchange factor gene locus, proteins, peptides (including dominant-negative peptides and antibodies), and the like.

According to the invention, agents that disrupt actin cytoskeletal organization are used excluding rho GTPase function inhibitors as agents useful in upregulating ecNOS activity. The invention can involve use of a rho GTPase function inhibitor (including a HMG-CoA reductase inhibitor), however, only if used together with an agent that disrupts actin cytoskeletal organization other than a rho GTPase function inhibitor.

HMG-CoA reductase inhibitors inhibit post-translational modifications of rho GTPases by preventing mevalonate synthesis and consequently geranylgeranylpyrophosphate synthesis, an isoprenoid that is attached to the CAAX motif of rho GTPases. Examples of HMG-CoA reductase inhibitors include some which are commercially available, such as simvastatin (U.S. Pat. No. 4, 444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622,985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302,604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S. Pat. No. 5,091,378, U.S. Pat. No. 4,904,646, U.S. Pat. No. 25 5,385,932, U.S. Pat. No. 5,250,435, U.S. Pat. No. 5,132,312, U.S. Pat. No. 5,130,306, U.S. Pat. No. 5,116,870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994,494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860, U.S. Pat. No. 4,940,800, U.S. Pat. No. 4,940,727, U.S. Pat. No. 4,939,143, U.S. Pat. No. 4,929,620, U.S. Pat. No. 4,923,861, U.S. Pat. No. 4,906,657, U.S. Pat. No. 4,906,624 and U.S. Pat. No. 4,897,402, the disclosures of which patents are incorporated herein by reference.

Other rho GTPase function inhibitors not described in the above categories and useful according to the invention include agents that inhibit rho GTPase activation via a receptor-mediated signaling pathway. Such agents include protein kinase C inhibitors, Gq protein inhibitors (e.g., C-terminal antibodies, dominant-negative Gq mutants, etc.), tyrosine kinase inhibitors (e.g., genistein, etc.), tyrosine phosphatase stimulators, GTPase-activating protein stimulators, inhibitors of integrins and adhesion molecules, adapter protein (Shc and Sos) inhibitors, and Pleckstrin homology domains which bind G-protein bg.

The invention also involves the co-administration of agents that are not agents that disrupt actin cytoskeletal organization but that can act cooperatively, additively or synergistically with such agents that disrupt actin cytoskeletal organization to increase ecNOS activity. Thus, ecNOS substrates which are converted by ecNOS to nitric oxide can be co-administered with the agents that disrupt actin cytoskeletal organization according to the invention. Such ecNOS substrates may be natural or synthetic, although the preferred substrate is L-arginine.

Likewise, there are other agents besides agents that disrupt actin cytoskeletal organization, that are not substrates of ecNOS, and that can increase ecNOS activity. Examples of categories of such agents are estrogens and ACE inhibitors. Estrogens are a well defined category of molecules known by those of ordinary skill in the art, and will not be elaborated upon further herein. All share a high degree of structural similarity. ACE inhibitors also have been well characterized, although they do not always share structural homology.

Angiotensin converting enzyme, or ACE, is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 5 4,512,924) and benazapril (U.S. Pat. No. 4,410,520), phosphinylalkanoyl prolines such as fosinopril (U.S. Pat. No. 4,337,201) and trandolopril.

Estrogens upregulate Nitric Oxide Synthase expression whereas ACE inhibitors do not affect expression, but instead influence the efficiency of the action of Nitric Oxide Synthase on L-arginine. Thus, activity can be increased in a variety of ways. In general, activity is increased by the reductase inhibitors of the invention by increasing the amount of the active enzyme present in a cell versus the amount present in a cell absent treatment with the reductase inhibitors according to the invention.

The invention also involves the co-administration of "at least one different agent that disrupts actin cytoskeletal organization" (second agent that disrupts actin cytoskeletal organization) that can act cooperatively, additively or synergistically with a first agent that disrupts actin cytoskeletal organization of the invention to increase ecNOS activity. Thus, "at least one different agent that disrupts actin cytoskeletal organization" is meant to include one or more agent(s) that disrupts actin cytoskeletal organization that is (are) different to the first agent that disrupts actin cytoskeletal organization of the invention and can include a HMG-CoA reductase inhibitor and/or a rho GTPase function inhibitor. In one embodiment, when the agent that disrupts actin cytoskeletal organization according to the invention is co-administered in combination with "at least one different agent that disrupts actin cytoskeletal organization" and the "at least one different agent that disrupts actin cytoskeletal organization" is a HMG-CoA reductase inhibitor, the subject is nonhypercholesterolemic.

The agents that disrupt actin cytoskeletal organization are administered in effective amounts. In general, an effective amount is any amount that can cause an increase in Nitric Oxide Synthase activity in a desired cell or tissue, and preferably in an amount sufficient to cause a favorable phenotypic change in a condition such as a lessening, alleviation or elimination of a symptom or of a condition.

In general, an effective amount is that amount of a pharmaceutical preparation that alone, or together with further doses or co-administration of other agents, produces the desired response. This may involve only slowing the progression of the disease temporarily, although more preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 50–500 mg/kg will be suitable, preferably orally and in one or several administrations per day.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents that disrupt actin cytoskeletal organization useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of reductase inhibitors, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

Other delivery systems can include time-release, delayed release or sustained release delivery systems. Such systems can avoid repeated administrations of the active compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and triglycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pats. Nos. 4,452,775, 4,667,014, 4,748,034 and 5,239,660 and (b) difusional systems in which an active component permeates at a controlled rate from a polymer such as described in U.S. Pats. Nos. 3,832,253, and 3,854,480. In addition, pump-based hardware delivery systems can be used, some of which are adapted for implantation.

Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

According to another aspect of the invention, a method for increasing blood flow in a tissue of a subject is provided. The method involves administering to a subject in need of such treatment a first agent that disrupts actin cytoskeletal organization in an amount effective to increase endothelial cell Nitric Oxide Synthase activity in the tissue of the subject, provided that the first agent is not a rho GTPase function inhibitor or fasudil. Fasudil (a substituted isoquinolinesulfonyl compound- also known as HA1077), described in U.S. Pat. No. 4,678,783 as a compound with vasodilating properties, was not known to act as an agent that disrupts actin cytoskeletal organization resulting in increased ecNOS expression prior to the present invention.

In important embodiments a second agent is co-administered to a subject with a condition treatable by the second agent in an amount effective to treat the condition, whereby the delivery of the second agent to a tissue of the subject is enhanced as a result of the increased blood flow from administering the first agent of the invention (an agent that disrupts actin cytoskeletal organization). The "second agent" may be any pharmacological compound or diagnostic agent, as desired.

Examples of catagories of pharmaceutical agents include: adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; antiemetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratblytic; LNRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine Al antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; treatment of amyotrophic lateral sclerosis; treatment of cerebral ischemia; treatment of Paget's disease; treatment of unstable angina; uricosuric; vasoconstrictor; vasodilator; vulnerary; wound healing agent; xanthine oxidase inhibitor.

In another aspect of the invention, the agent that disrupts actin cytoskeletal organization is "co-administered," which means administered substantially simultaneously with another agent. By substantially simultaneously, it is meant that the agent that disrupts actin cytoskeletal organization is administered to the subject close enough in time with the administration of the other agent, whereby the two compounds may exert an additive or even synergistic effect, i.e. on increasing ecNOS activity or on delivering a second agent to a tissue via increased blood flow.

EXAMPLES

"Upregulation of Endothelial Cell Nitric Oxide Synthase by HMG CoA Reductase Inhibitors"

Experimental Procedures:

All standard culture reagents were obtained from JRH Bioscience (Lenexa, Kans.). Unless indicated otherwise, all reagents were purchased from Sigma Chemical Co. (St. Louis, Mo.). [a-$^{32}$P]CTP (3000 Ci/mmol) was supplied by New England Nuclear. Purified human LDL was obtained from Calbiochem (San Diego, Calif.; lot#730793) and Biomedical Technologies Inc. (Stoughton, Mass.; lot#90301 97). The level of endotoxin was determined by the chromogenic Limulus amebocyte assay (BioWhittaker Inc., Walkersville, Md.). The antibody detection kit (Enhanced Chemiluminescence) and the nylon nucleic acid (Hybond) and protein (PVDF) transfer membranes were purchased from Amersham Corp. (Arlington Heights, Ill.). Simvastatin and lovastatin were obtained from Merck, Sharp, and Dohme, Inc. (West Point, Pa.). Since endothelial cells lack lactonases to process simvastatin and lovastatin to their active forms, these HMG-CoA reductase inhibitors were chemically activated prior to their use with methods well known in the art and as previously described (Laufs, U et al., *J Biol Chem*, 1997, 272:31725–31729).

Cell Culture:

Human endothelial cells were harvested from saphenous veins and cultured as described (15). For transfection studies, bovine aortic endothelial cells of less than 3 passages were cultured in a growth medium containing DMEM (Dulbecco's Modified Eagle's Medium), 5 mmol/L L-glutamine (Gibco), and 10% fetal calf serum (Hyclone Lot #1114577). For all experiments, the endothelial cells were placed in 10% lipoprotein-deficient serum (Sigma, Lot #26H9403 1) for 48 h prior to treatment conditions. In the indicated experiments, endothelial cells were pretreated with actinomycin D (5 mg/ml) for 1 h prior to treatment with ox-LDL and/or simvastatin. Cellular viability as determined by cell count, morphology, and Trypan blue exclusion was maintained for all treatment conditions.

Preparation of LDL:

The LDL was prepared by discontinuous ultracentrifugation according to the method of Chung et al. with some modification (*Methods Enzymol*, 1984, 128:181–209). Fresh plasma from a single donor was anticoagulated with heparin and filtered through a Sephadex G-25 column equilibrated with PBS. The density was adjusted to 1.21 g/ml by addition of KBr (0.3265 g/ml plasma). A discontinuous NaCl/KBr gradient was established in Beckman Quick-Seal centrifuge tubes (5.0 ml capacity) by layering 1.5 ml of density-adjusted plasma under 3.5 ml of 0.154 M NaCl in Chelex-100-treated water (BioRad, Hercules, Calif.). After ultracentrifugation at 443,000×g and 7° C. for 45 min in a Beckman Near Vertical Tube 90 rotor (Beckman L8-80M ultracentrifuge), the yellow band in the upper middle of the tube corresponding to LDL was removed by puncturing with a needle and withdrawing into a syringe. The KBr was removed from the LDL by dialyzing with three changes of sterile PBS, pH 7.4, containing 100 μg/ml polymyxin B.

The purity of the LDL samples was confirmed by SDS/polyacrylamide and cellulose acetate gel electrophoresis. Cholesterol and triglyceride content were determined as previously described (Liao, J K et al., *J Biol Chem*, 1995, 270:319–324.). The LDL protein concentration was determined by the method of Lowry et al., (*J Biol Chem*, 1951, 193:265–275.). For comparison, commercially-available LDL (Biomedical Technologies Inc., Stoughton, Mass.; Calbiochem, San Diego, Calif.) were characterized and used in selected experiments.

Oxidation of LDL:

Oxidized LDL was prepared by exposing freshly-isolated LDL to $CuSO_4$ (5–10 mM) at 37° C. for various duration (6–24 h). The reaction was stopped by dialyzing with three changes of sterile buffer (150 μmol/L NaCl, 0.01% EDTA and 100 μg/ml polymyxin B, pH 7.4) at 4° C. The degree of LDL oxidation was estimated by measuring the amounts of thiobarbituric acid reactive substances (TBARS) produced using a fluorescent assay for malondialdehyde as previously described (Yagi, K A, *Biochem Med*, 1976, 15:212–21.). The extent of LDL modification was expressed as nanomoles of malondialdehyde per mg of LDL protein. Only mild to moderate ox-LDL with TBARS values between 12 and 16 nmol/mg LDL protein (i.e. 3 to 4 nmol/mg LDL cholesterol) were used in this study. All oxidatively-modified LDL samples were used within 24 h of preparation.

Northern Blotting:

Equal amounts of total RNA (10–20 mg) were separated by 1.2% formaldehyde-agarose gel electrophoresis and transferred overnight onto Hybond nylon membranes. Radiolabeling of human full-length ecNOS cDNA (Verbeuren, T J et al., *Circ Res*, 1986, 58:552–564, Liao, J K et al., *J Clin Invest*, 1995, 96:2661–2666) was performed using random hexamer priming, [a-$^{32}$P]CTP, and Kienow (Pharmacia). The membranes were hybridized with the probes overnight at 45° C. in a solution containing 50% formamide, 5×SSC, 2.5×Denhardt's Solution, 25 mM sodium phosphate buffer (pH 6.5), 0.1% SDS, and 250 mg/ml salmon sperm DNA. All Northern blots were subjected to stringent washing conditions (0.2 ×SSC/0.1% SDS at 65° C.) prior to autoradiography. RNA loading was determined by rehybridization with human GAPDH probe.

Western Blotting:

Cellular proteins were prepared and separated on SDS/PAGE as described (Liao, J K et al., *J Biol Chem*, 1995, 270:319–324). Immunoblotting was performed using a murine monoclonal antibody to human ecNOS (1:400 dilution, Transduction Laboratories, Lexington, Ky.). Immunodetection was accomplished using a sheep anti-mouse secondary antibody (1:4000 dilution) and the enhanced chemiluminescence (ECL) kit (Amersham Corp., Arlington Heights, Ill.). Autoradiography was performed at 23° C. and the appropriate exposures were quantitated by densitometry.

Assay for ecNOS Activity:

The ecNOS activity was determined by a modified nitrite assay as previously 10 described (Misko, T P et al., *Analytical Biochemistry*, 1993, 214:11–16, Liao, J K et al., *J Clin Invest*, 1995, 96:2661–2666). Briefly, endothelial cells were treated for 24 h with ox-LDL in the presence and absence of simvastatin (0.1 to 1 mM). After treatment, the medium was removed, and the cells were washed and incubated for 24 h in phenol red-free medium. After 24 h, 300 μl of conditioned medium was mixed with 30 μl of freshly prepared 2,3-diaminonaphthalene (1.5 mmol/L DAN in 1 mol/L HCl). The mixture was protected from light and incubated at 20° C. for 10 min. The reaction was terminated with 15 μl of 2.8 mol/L NaOH. Fluorescence of 1-(H)-naphthotriazole was measured with excitation and emission wavelengths of 365 and 450 nm, respectively. Standard curves were constructed with known amounts of sodium nitrite. Nonspecific fluorescence was determined in the presence of LNMA (5 mmol/L).

Nuclear Run-on Assay:

Confluent endothelial cells (~5×10$^7$ cells) grown in LPDS were treated with simvastatin (1 mM) or 95% $O_2$ for 24 h. Nuclei were isolated and in vitro transcription was performed as previously described (Liao, J K et al., *J Clin*

*Invest*, 1995, 96:2661–2666). Equal amounts (1 mg) of purified, denatured full-length human ecNOS, human b-tubulin (ATCC #37855), and linearized pGEM-3z cDNA were vacuum-transferred onto nitrocellulose membranes using a slot blot apparatus (Schleicher & Schuell). Hybridization of radiolabeled mRNA transcripts to the nitrocellulose membranes was carried out at 45° C. for 48 h in a buffer containing 50% formamide, 5×SSC, 2.5×Denhardt's solution, 25 mM sodium phosphate buffer (pH 6.5), 0.1% SDS, and 250 mg/ml salmon sperm DNA. The membranes were then washed with 1×SSC/0.1% SDS for 1 h at 65° C. prior to autoradiography for 72 h at −80° C.

Transfection Assays:

For transient transfections, bovine rather than human endothelial cells were used because of their higher transfection efficiency by the calcium-phosphate precipitation method (12% vs <4%) (Graham, F L and Van der Erb, A *J, Virology*, 1973, 52:456–457). We used the human ecNOS promoter construct, F1.LUC, which contains a −1.6 kb 5'-upstream sequence linked to the luciferase reporter gene as described by Zhang et al. (*J Biol Chem*, 1995, 270:15320–15326). Bovine endothelial cells (60%–70% confluent) were transfected with 30 mg of the indicated constructs: p.LUC (no promoter), pSV2.LUC (SV40 early promoter), or F1.LUC. As an internal control for transfection efficiency, pCMV.bGal plasmid (10 mg) was co-transfected in all experiments. Preliminary results using b-galactosidase staining indicate that cellular transfection efficiency was approximately 10% to 14%.

Endothelial cells were placed in lipoprotein-deficient serum for 48 h after transfection and treated with ox-LDL (50 mg/ml, TBARS 12.4 nmol/mg) in the presence and absence of simvastatin (1 mM) for an additional 24 h. The luciferase and b-galactosidase activities were determined by a chemiluminescence assay (Dual-Light, Tropix, Bedford, Mass.) using a Berthold L9501 luminometer. The relative promoter activity was calculated as the ratio of luciferase- to b-galactosidase activity. Each experiment was performed three times in triplicate.

Data Analysis:

Band intensities were analyzed densitometrically by the National Institutes of Health Image program (Rasband, W, NIH Image program, v 1.49, National Institutes of Health, Bethesda, 1993). All values are expressed as mean+SEM compared to controls and among separate experiments. Paired and unpaired Student's t tests were employed to determine any significant changes in densitometric values, nitrite production, and promoter activities. A significant difference was taken for P values less than 0.05.

Example 1

Cell Culture

Relatively pure (>95%) human endothelial cell cultures were confirmed by their morphological features (i.e. cuboidal, cobble-stone, contact inhibited) using phase-contrast microscopy and by immunofluorescent staining with anti-Factor VIII antibodies (Gerson, R J et al., *Am J Med*, 1989, 87:28–38). For all experimental conditions, there were no observable adverse effects of ox-LDL or HMG-CoA reductase inhibitors on cellular morphology, cell number, immunofluorescent staining, and Trypan blue exclusion (>95%). Higher concentrations of ox-LDL (>100 mg/ml) with greater oxidative modification (i.e. TBARS values of >30 nrnol/mg) caused vacuolization and some detachment of endothelial cells after 24 h. Neither simvastatin (0.01 to 0.1 mmol/L) nor lovastatin (10 mmol/L) produced any noticeable adverse effects on human endothelial cell for up to 96 h. However, higher concentrations of simvastatin (>15 mmol/L) or lovastatin (>50 mmol/L) caused cytotoxicity after 36 h, and therefore, were not used.

Example 2

Characterization of LDL

SDS/polyacrylamide gel electrophoresis of native or unmodified LDL revealed a single band (∼510 kD) corresponding to ApoB-100 (data not shown). Similarly, cellulose acetate electrophoresis revealed only one band corresponding to the presence of a single class of low-density lipids (density of 1.02 to 1.06 g/ml). The LDL had a protein, cholesterol, and triglyceride concentration of 6.3±0.2, 2.5±0.1, and 0.5±0.1 mg/ml, respectively. In contrast, lipoprotein-deficient serum was devoid of both apob-100 protein and low-density lipid bands, and had non-detectable levels of cholesterol. There was no detectable level of endotoxin (<0.10 EU/ml) in the lipoprotein-deficient serum or ox-LDL samples by the chromogenic Limulus amebocyte assay.

In addition, there was no apparent difference between our own preparation and commercially-obtained LDL samples in terms of electrophoretic mobility. Native LDL had a TBARS value of 0.3±0.2 nmol/mg, but after exposure to human saphenous vein endothelial cells in lipoprotein-deficient media for 72 h, this value increased to 3.1±0.4 nmol/mg. Copper-oxidized LDL had TBARS values ranging from 4.6±0.5 to 33.1±5.2 nmol/mg. The degree of ox-LDL used in this study was mild to moderate with TBARS value ranging from 12 to 16 nmol/mg LDL protein (i.e. 3 to 4 nmol/mg LDL cholesterol).

Example 3

Effect of ox-LDL and HMG-CoA Reductase Inhibitors on ecNOS Protein

We have previously shown that ox-LDL (50 mg/ml) downregulates ecNOS expression (Liao, J K et al., *J Biol Chem*, 1995, 270:319–324). Compared to untreated cells, treatment with ox-LDL (50 mg/ml, TBARS 12.2 nmol/mg) caused a 54%±6% decrease in ecNOS protein after 48 h (p<0.01, n=4). There was no difference between our preparation of ox-LDL and commercially-available ox-LDL with similar TBARS values in terms of the degree of ecNOS downregulation. Addition of simvastatin (0.01 mmol/L) did not significantly affect he downregulation of ecNOS protein by ox-LDL (57%±8% decrease, p>0.05, n=4). However, in the presence of 0.1 mmol/L of simvastatin, ox-LDL no longer produce any significant decrease in ecNOS protein levels (4%±7% decrease, p<0.01, n=4). Higher concentrations of simvastatin (1 and 10 mmol/L) resulted in not only a reversal of ecNOS downregulation by ox-LDL, but also significant increases in ecNOS protein levels above baseline (146%±9% and 210%±12%, respectively, p<0.05, n=4). Simvastatin or lovastatin (10 mmol/L) which were not chemically-activated had no effect on ecNOS expression.

In a time-dependent manner, treatment with ox-LDL (50 mg/ml, TBARS 12.2 nmol/mg) decreased ecNOS protein expression by 34% (5%, 67% (8% and 86 (5% after 24 h, 72 h, and 96 h, respectively (p<0.05 for all values; n=4,). Compared to ox-LDL alone, co-treatment with simvastatin (0.1 mmol/L) attenuated the decrease in ecNOS protein level after 24 h (15% (2% vs 34% (5%, p<0.05, n=4). Longer incubation with simvastatin (0.1 mmol/L) for 72 h and 96 h not only reversed ox-LDL's inhibitory effects on ecNOS expression, but also increased ecNOS protein levels by 110% (6% and 124% (6% above basal expression (p<0.05, n=4). Thus, compared to ox-LDL alone, co-treatment with simvastatin produced a 1.3-, 3.3- and 8.9-fold increase ecNOS protein levels after 24 h, 72 h, and 96 h, respectively.

Example 4

Effect of ox-LDL and HMG-CoA Reductase Inhibitors on ecNOS mRNA

The effect of simvastatin on ecNOS mRNA levels occurred in a time-dependent manner and correlated with its effect on ecNOS protein levels. Northern analyses showed that ox-LDL (50 mg/ml, TBARS 15.1 nmol/mg) produced a time-dependent 65±5% and 91±4% decrease in ecNOS mRNA levels after 48 h and 72 h, respectively (p<0.01, n=3). Compared to ox-LDL at the indicated time points, co-treatment with simvastatin 0.1 mmol/L) increased ecNOS mRNA levels by 6.3-fold after 48 h and 14.5-fold after 72 h (p<0.01 for all values, n=3).

To determine whether treatment with another HMG-CoA reductase inhibitor have similar effect as simvastatin, we treated endothelial cells with lovastatin. Again, ox-LDL decreased steady-state ecNOS mRNA by 52±5% after 24 h (p<0.01, n=3). Treatment with lovastatin (10 mmol/L) not only reversed the inhibitory effects of ox-LDL on ecNOS mRNA, but also caused a 40±9% increase in ecNOS mRNA level compared to that of untreated cells. Compared to ox-LDL alone, co-treatment with lovastatin caused a 3.6-fold increase in ecNOS mRNA levels after 24 h. Treatment with lovastatin alone, however, produced 36% increase in ecNOS mRNA levels compared to untreated cells (p<0.05, n=3).

Example 5

Effect of ox-LDL and Simvastatin on ecNOS Activity

The activity of ecNOS was assessed by measuring the LNMA-inhibitable nitrite production from human endothelial cells (Liao, J K et al., *J Clin Invest*, 1995, 96:2661–2666). Basal ecNOS activity was 8.8±1.4 nmol/500,000 cells/24 h. Treatment with ox-LDL (50 mg/ml, TBARS 16 nmol/mg) for 48 h decreased ecNOS-dependent nitrite production by 94±3% (0.6±0.5 nmol/500,000 cells/24 h, p<0.001). Co-treatment with simvastatin (0.1 mmol/L) significantly attenuated this downregulation resulting in a 28±3% decrease in ecNOS activity compared to untreated cells (6.4±0.3 nmol/500,000 c cells/24 h, p<0.05). Co-treatment with a higher concentration of simvastatin (1 mmol/L) not only completely reversed the downregulation of ecNOS by ox-LDL, but also, resulted in a 45±6% increase in ecNOS activity compared to baseline (12.8±2.7 nmol/500,000 cells/24 h, p<0.05).

Example 6

Effect of Simvastatin on ecNOS mRNA Stability

The post-transcriptional regulation of ecNOS mRNA was determined in the presence of the transcriptional inhibitor, actinomycin D (5 mg/ml). Oxidized LDL (50 mg/ml, TBARS 13.1 nmol/mg) shortened the half-life of ecNOS mRNA (t1/2 35±3 h to 14±2 h, p<0.05, n=3). Co-treatment with simvastatin (0.1 mmol/L) prolonged the half-life of ecNOS mRNA by 1.6-fold (t1/2 22±3 h, p<0.05, n=3). Treatment with simvastatin alone prolonged ecNOS mRNA half-life by 1.3-fold over baseline (t1/2 43±4 h, p<0.05, n=3).

Example 7

Effect of Simvastatin on ecNOS Gene Transcription

To determine whether the effects of simvastatin on ecNOS expression occurs at the level of ecNOS gene transcription, we performed nuclear run-on assays using endothelial cells treated with simvastatin (1 mmol/L) for 24 h. Preliminary studies using different amounts of radiolabelled RNA transcripts demonstrate that under our experimental conditions, hybridization was linear and nonsaturable. The density of each ecNOS band was standardized to the density of its corresponding b-tubulin. The specificity of each band was determined by the lack of hybridization to the nonspecific pGEM cDNA vector. In untreated endothelial cells (control), there was constitutive ecNOS transcriptional activity (relative index of 1.0). Treatment with simvastatin (1 mmol/L) did not significantly affect ecNOS gene transcription compared to that of untreated cells (relative index of 1.2±0.3, p>0.05, n=4). However, treatment of endothelial cells with hyperoxia (95%$_{O2}$) significantly increased ecNOS gene expression (relative index of 2.5, p<0.05, n=4).

To further confirm the effects of simvastatin on ecNOS gene transcription by a different method, we transfected bovine aortic endothelial cells using a −1600 to +22 nucleotide ecNOS 5'-promoter construct linked to a luciferase reporter gene (F1.LUC) (Zhang, R et al., *J Biol Chem*, 1995, 270:15320–15326). This promoter construct contains putative cis-acting elements for activator protein (AP)-1 and -2, sterol regulatory element-1, retinoblastoma control element, shear stress response element (SSRE), nuclear factor-1 (NF-1), and cAMP response element (CRE). Treatment with ox-LDL (50 mg/ml, TBARS 14.5 nmol/mg), simvastatin (1 µmol/L), alone or in combination, did not significantly affect basal F1 promoter activity. However, laminar fluid shear-stress (12 dyneslcm2 for 24 h) was able to induce F1 promoter activity by 16-fold after 24 h (data not shown) indicating that the F1 promoter construct is functionally-responsive if presented with the appropriate stimulus.

Example 8

Effect of Simvastatin and Lovastatin on ecNOS Expression

To further characterize the effects of HMG-CoA reductase inhibitors on the upregulation ecNOS expression, we treated endothelial cells with simvastatin (0.1 mmol/L) for various durations (0–84 h). Treatment with simvastatin (0.1 mmol/L) increased ecNOS protein levels by 4 (6%, 21 (9%, 80 (8%, 90 (12%, and 95 (16% after 12 h, 24 h, 48 h, 72 h, and 84 h, respectively (p<0.05 for all time points after 12 h, n=4). Higher concentrations of simvastatin similarly increased ecNOS protein levels, but in significantly less time compared to lower concentrations of simvastatin (data not shown).

In a concentration-dependent manner, treatment with simvastatin (0.01 to 10 mmol/L, 48 h) increased ecNOS expression by 1 (6%, 80 (8%, 190 (10% and 310 (20%, respectivel (p<0.05 for concentrations (0.1 mmol/L, n=4). The upregulation of ecNOS expression by simvastatin, therefore, is dependent upon both the concentration and duration of simvastatin treatment. For comparison, treatment with lovastatin (0.1 to 10 mmol/L, 48 h) also increased ecNOS expression in a concentration-dependant manner (10 (6%, 105 (8% and 180 (11%, respectively, $p<0.05$ for concentrations $>0.1$ mmol/L, n=3) but significantly less effectively than simvastatin at comparable concentrations. Therefore, at the same concentration, simvastatin had greater effects on ecNOS expression compared to lovastatin. These results are consistent with reported IC50 values for simvastatin and lovastatin (4 nmol/L and 19 nmol/L, respectively) (Van Vliet, A K et al., *Biochem Pharmacol*, 1996, 52:1387–1392).

Example 9

Effect of L-Mevalonate on ecNOS Expression

To confirm that the effects of simvastatin on ecNOS expression were due to the inhibition of endothelial HMG CoA reductase, endothelial cells were treated with ox-LDL (50 mg/ml, TBARS 15.1 nmol/mg), simvastatin (1 mmol/L), alone or in combination, in the presence of L-mevalonate (100 mmol/L). Treatment with ox-LDL decreased ecNOS expression by 55% (6% after 48 h which was completely reversed and slightly upregulated in the presence of simvastatin (1 mmol/L) (150% (8% above basal expression) ($p<0.05$ for both, n=3).

Compared to endothelial cells treated with ox-LDL and simvastatin, addition of L-mevalonate reduced ecNOS protein by 50%±5% ($p<0.05$, n=3). Furthermore, the upregulation of ecNOS expression by simvastatin alone (2.9-fold increase, $p<0.05$, n=3) was completely reversed by co-treatment with L-mevalonate. Treatment with L-mevalonate alone did not have any appreciable effects on basal ecNOS expression ($p>0.05$, n=3). Similar findings were also observed with L-mevalonate and lovastatin.

"HMG-CoA Reductase Inhibitors Reduce Cerebral Infarct Size by Upregulating endothelial cell Nitric Oxide Synthase"

Experimental Procedures

Cell Culture:

Human endothelial cells were harvested from saphenous veins using Type II collagenase (Worthington Biochemical Corp., Freehold, N.J.) as previously described. Cells of less than three passages were grown to confluence in a culture medium containing Medium 199, 20 mM HEPES, 50 mg/ml ECGS (Collaborative Research Inc., Bedford, Ma.), 100 mg/ml heparin sulfate, 5 mM L-glutamine (Gibco), 5% fetal calf serum (Hyclone, Logan, UT), and antibiotic mixture of penicillin (100 U/ml)/ streptomycin (100 mg/ml)/Fungizone (1.25 mg/ml). For all experiments, the endothelial cells were grown to confluence before any treatment conditions. In some experiments, cells were pretreated with actinomycin D (5 mg/ml) for 1 h prior to treatment with HMG-CoA reductase inhibitors.

Exposure of Endothelial Cells to Hypoxia:

Confluent endothelial cells grown in 100 mm culture dishes were treated with HMG-CoA reductase inhibitors and then placed without culture dish covers in humidified airtight incubation chambers (Billups-Rothenberg, Del Mar, Calif.). The chambers were gassed with 20% or 3% $O_2$, 5% $CO_2$, and balanced nitrogen for 10 min prior to sealing the chambers. The chambers were maintained in a 37° C. incubator for various durations (0–48 h) and found to have less than 2% variation in $O_2$ concentration as previously described (Liao, J K et al., *J Clin Invest*, 1995, 96:2661–2666). Cellular confluence and viability were determined by cell count, morphology, and trypan blue exclusion.

In vitro Transcription Assay:

Confluent endothelial cells ($5 \times 10^7$ cells were treated with simvastatin (1 mM) in the presence of 20% or 3% $O_2$ for 24 h. Nuclei were isolated and in vitro transcription was performed as previously described (Liao, J K et al., *J Clin Invest*, 1995, 96:2661–2666). Equal amounts (1 mg) of purified, denatured full-length human ecNOS, human b-tubulin (ATCC #37855), and linearized pGEM-3z cDNA were vacuum-transferred onto nitrocellulose membranes using a slot blot apparatus (Schleicher & Schuell). Hybridization of radiolabeled mRNA transcripts to the nitrocellulose membranes was carried out at 45° C. for 48 h in a buffer containing 50% formamide, 5×SSC, 2.5×Denhardt's solution, 25 mM sodium phosphate buffer (pH 6.5), 0.1% SDS, and 250 mg/ml salmon sperm DNA. The membranes were then washed with 1×SSC/0.1% SDS for 1 h at 65° C. prior to autoradiography for 72 h at −80° C. Band intensities were subjected to analyses by laser densitometry.

Assay for Nitrite Accumulation:

The amount of NO produced by ecNOS was determined by nitrite accumulation in the conditioned medium. Nitrite accumulation was determined by measuring the conversion of 2,3-diaminonaphthalene (1.5 mM of DAN in 1 M of HCl) and nitrite to 1-(H)-naphthotriazole as previously described (13,24). Nonspecific fluorescence was determined in the presence of LNMA (5 mM). Previous studies with nitrate reductase indicate that the nitrite to nitrate concentration in the medium was approximately 5:1 and that this ratio did not vary with exposure to 20% or 3% $O_2$ concentration.

Murine Model of Cerebral Vascular Ischemia

Adult male (18–20 g) wildtype SV-129 mice (Taconic farm, Germantown, N.Y.) and ecNOS mutant mice (Huang, P L et al., *Nature*, 1995, 377:239–242.) were subcutaneously injected with 0.2, 2, or 20 mg of activated simvastatin per kg body weight or saline (control) once daily for 14 days. Ischemia was produced by occluding the left middle cerebral artery (MCA) with a coated 8.0 nylon monofilament under anesthesia as described (Huang, Z et al., *J Cereb Blood Flow Metab*, 1996, 16:981–987, Huang, Z et al., *Science*, 1994, 265:1883–1885, Hara, H et al., *J Cereb Blood Flow Metab*, 1997, 1:515–526). Arterial blood pressure, heart rate, arterial oxygen pressure, and partial pressure of carbon dioxide were monitored as described (Huang, Z et al.,*J Cereb Blood Flow Metab*, 1996, 16:981–987, Huang, Z et al., *Science*, 1994, 265:1883–1885, Hara, H et al., *J Cereb Blood Flow Metab*, 1997, 1:515–526). The filaments were withdrawn after 2 hours and after 24 h, mice were either sacrificed or tested for neurological deficits using a well-established, standardized, observer-blinded protocol as described (Huang, Z et al., *J Cereb Blood Flow Metab*, 1996, 16:981–987, Huang, Z et al., *Science*, 1994, 265:1883–1885, Hara, H et al., *J Cereb Blood Flow Metab*, 1997, 1:515–526). The motor deficit score range from 0 (no deficit) to 2 (complete deficit).

Brains were divided into five coronal 2-mm sections using a mouse brain matrix (RBM-200C, Activated Systems, Ann Arbor, Mich., USA). Infarction volume was quantitated with an image analysis system (M4, St. Catharines, Ontario, Canada) on 2% 2,3,5-triphenyltetrazolium chloride stained 2-mm slices. The levels of serum cholesterol, creatinine and transaminases were determined by the Tufts University Veterinary Diagnostic Laboratory (Grafton, Mass.).

Assay for ecNOS Activity from Tissues:

The ecNOS activities in mice aortae and brains were measured by the conversion of [$^3$H]arginine to [$^3$H]citrulline in the presence and absence of LNMA (5 mM) as described earlier.

Quantitative Reverse Transcription-Polymerase Chain Reaction:

Total RNA from mouse aortae and brains was isolated by the guanidinium isothiocyanate method and reverse transcribed using oligo-dT (mRNA Preamplification reagents; Gibco BRL) and Taq ploymerase (Perkin-Elmer). One tenth of the sDNA was used as template for the PCR reaction. Approximately 0.2 nmol of the following primers amplifying a 254-bp fragment of murine ecNOS cDNA were used: 5'Primer: 5'-GGGCTCCCTCCTTCCGGCTGCCACC-3' (SEQ ID NO. 1) and 3'Primer: 5'-GGATCCCTGGAAAAGGCGGTGAGG-3' (SEQ ID NO. 2) (Hara, H et al., *J Cereb Blood Flow Metab*, 1997, 1:515–526). For amplification of glyceraldehyde 3-phosphate dehydrogenase (GAPDH), 0.1 nmol of the following primers amplifying a 452-bp fragment were used: 5'Primer: 5'-ACCACAGTCCATGCCATCAC-3' (SEQ ID NO. 3) and 3' Primer: 5'-TCCACCACCCTGTTGCTGTA-3'(SEQ ID NO. 4). Denaturing was performed at 94° C. for 30 s, annealing at 60° C. for 30 s, and elongation at 72° C. for 60 s. Preliminary results indicated that the linear exponential phase for ecNOS and GAPDH polymerization was 30–35 cycles and 20–25 cycles, respectively.

Example 10

Cell Culture

Relatively pure (>98%) human saphenous vein endothelial cell cultures were confirmed by their morphological features (ie. cuboidal, cobble-stone, contact inhibited) using phase-contrast microscopy and immunofluorescent-staining with antibodies to Factor VIII. There were no observable adverse effects of HMG-CoA reductase inhibitors, L-mevalonic acid, or hypoxia on cellular morphology. However, higher concentrations of simvastatin (>15 mmol/L) or lovastatin (>50 mmol/L) caused cytotoxicity after 36 h, and therefore, were not used. Otherwise, cellular confluency and viability as determined by trypan blue exclusion were maintained for all treatment conditions described.

Example 11

Effects of HMG-CoA Reductase Inhibitors on ecNOS Activity

The activity of ecNOS was assessed by measuring the LNMA-inhibitable nitrite accumulation from human endothelial cells (Liao, J K et al., *J Clin Invest*, 1995, 96:2661–2666). The ratio of nitrite to nitrate production under our culture condition was approximately 5:1 and was similar for hypoxia and normoxia (data not shown). Basal ecNOS activity at 20% $O_2$ was 6.0±3.3 nmol/500,000 cells/24 h. Exposure of endothelial cells to 3% $O_2$ for 24 h decreased nitrite production by 75±14% (1.5±0.9 nmol/500,000 cells/24 h, p<0.01). Treatment with simvastatin (1 mM) not only completely reversed the downregulation of ecNOS by hypoxia, but resulted in a 3-fold increase in ecNOS activity over basal activity (18±5.0 nmol/500,000 cells/24 h, p<0.05). This upregulation of ecNOS activity was attenuated by the addition of L-mevalonate (400 mM) (9.6±1.3 nmol/500,000 cells/24 h, p<0.05). Interestingly, simvastatin (1 mM) alone upregulated nitrite production 5-fold (30±6.5 nmol/500,000 cells/24 h, p<0.01), which was completely blocked by L-mevalonate (400 mM) (8.6±2.9 nmol/500,000 cells/24 h, p<0.05). Similar findings were observed with lovastatin, but at 10-fold higher concentration compared to that of simvastatin.

Example 12

Effects of HMG-CoA Reductase Inhibitors on ecNOS Protein and mRNA Levels

In a concentration-dependent manner, treatment with simvastatin (0.01 to 10 mM, 48 h) increased ecNOS expression by 1 (6%, 80 (8%, 190 (10% and 310 (20%, respectively (p<0.05 for concentrations (0 mM, n=4). Treatment with simvastatin (0.1 mM) increased ecNOS protein levels in a time-dependent manner by 4 (6%, 21 (9%, 80 (8%, 90 (12%, and 95 (16% after 12 h, 24 h, 48 h, 72 h, and 84 h, respectively (p<0.05 for all time points 12 h, n=4) (data not shown). Another HMG-CoA reductase inhibitor, lovastatin, also increased ecNOS protein levels in a time-, and concentration-dependent manner (data not shown). Because lovastatin has a higher IC50 value for HMG-CoA reductase compared to that of simvastatin, it was 10-fold less potent in upregulating ecNOS protein levels than simvastatin at equimolar concentrations.

We have previously shown that hypoxia downregulates ecNOS protein expression (Liao, J K et al., *J Clin Invest*, 1995, 96:2661–2666). Compared to normoxia (20% $O_2$), exposure to hypoxia (3% $O_2$) resulted in a 46±4 % and 75±3 % reduction in ecNOS protein levels after 24 h and 48 h, respectively (p<0.01, n=3). In a concentration-dependent manner, treatment with simvastatin produced a progressive reversal of hypoxia-mediated downregulation of ecNOS protein levels after 48 h. At higher concentrations of simvastatin (1 and 10 mM), ecNOS protein levels were upregulated to 159±13 % and 223±21 % of basal levels (p<0.05, n=3). Co-treatment with L-mevalonic acid (400 mM) completely blocked simvastatin-induced increase in ecNOS protein levels after 48 h (35±2.4 %). Treatment with L-mevalonic acid alone, however, did not produce any significant effects on basal ecNOS protein levels in untreated cells exposed to hypoxia (25±3.9 %, p>0.05, n=3). In addition, simvastatin which was not chemically-activated had no effect on ecNOS expression. These results indicate that simvastatin- and lovastatin-mediated increases in ecNOS protein expression are mediated by inhibition of endothelial HMG-CoA reductase.

To determine whether changes in ecNOS protein levels are due to changes in ecNOS steady-state mRNA levels, we performed Northern blotting on endothelial cells exposed to normoxia and hypoxia in the presence or absence of simvastatin (1 mM) and lovastatin (10 $\mu$M). Simvastatin alone increased ecNOS mRNA levels to 340±24 % (p<0.01, n=3). Exposure of endothelial cells to hypoxia reduced ecNOS mRNA levels by 70%+2 % and 88±4% after 24 h and 48 h with respect to GAPDH mRNA levels, respectively. Co-treatment with simvastatin not only completely reversed hypoxia-mediated decrease in ecNOS mRNA levels, but increased ecNOS mRNA levels to 195±12 % and 530±30% of basal levels after 24 h and 48 h, respectively (p<0.01, n=3). Similarly, lovastatin (10 $\mu$M) alone increased ecNOS message to 350±27 % under hypoxia and 410±21 % alone (p<0.01, n=3). Neither simvastatin nor lovastatin caused any significant change in G-protein as and b-actin mRNA levels under normoxic or hypoxic conditions. These results indicate that the effects of HMG-CoA reductase inhibitors are relatively selective in terms of their effects on ecNOS mRNA expression.

Example 13

Effects of HMG-CoA Reductase Inhibitors on ecNOS mRNA Half-life

The half-life of ecNOS mRNA was determined in the presence of actinomycin D (5 mg/ml). Hypoxia shortened the half-life of ecNOS mRNA from 28±4 h to 13±3 h. Treatment with simvastatin (1 mM) increased ecNOS half-life to 46±4 h and 38±4 h under normoxic and hypoxic conditions, respectively (p<0.05 for both, n=3). These results suggest that HMG-CoA reductase inhibitors prevent hypoxia-mediated decrease in ecNOS expression by stabilizing ecNOS mRNA.

Example 14

Effects of HMG-CoA Reductase Inhibitors on ecNOS Gene Transcription

Nuclear run-on assays showed that hypoxia caused a 85±8% decrease in ecNOS gene transcription (p<0.01, n=3). Treatment with simvastatin (1 mM) did not produce any significant affect on hypoxia-mediated decrease in ecNOS gene transcription (83±6% decrease in ecNOS gene transcription, p>0.05 compared to hypoxia alone). Furthermore, simvastatin alone produced minimal increase in ecNOS gene transcription under normoxic condition (20±5% increase in ecNOS gene transcription, p<0.05 compared to normoxia control).

Preliminary studies using different amounts of radiolabeled RNA transcripts demonstrate that under our experimental conditions, hybridization was linear and nonsaturable. The density of each ecNOS band was standardized to the density of its corresponding (b-tubulin band, relative intensity). To exclude the possibility that changes in (b-tubulin gene transcription are caused by hypoxia or simvastatin, another gene, GAPDH, was included on each of the nuclear run-on blots. Similar relative indices were obtained when ecNOS gene transcription was standardized to GAPDH gene transcription. The specificity of each band was determined by the lack of hybridization to the nonspecific pGEM cDNA vector.

Example 15

Effect of HMG-CoA Reductase Inhibitors on Mouse Physiology

To determine whether the upregulation of ecNOS by HMG-CoA reductase inhibitors occurs in vivo, SV-129 wild-type and ecNOS knockout mice were treated with 2 mg/kg simvastatin or saline subcutaneously for 14 days (n=8). The mean arterial blood pressures of wild-type and ecNOS mutant mice were as reported previously (Huang, P L ct al., Nature, 1995, 377:239–242). The ecNOS mutants were relatively hypertensive. There was no significant change in mean arterial blood pressures of wild-type mice after 14 days of simvastatin treatment (81±7 mmHg vs. 93±10 mmHg, p>0.05). There was also no significant group difference in heart rate, arterial blood gases and temporalis muscle temperature before ischemia or after reperfusion. Furthermore, there was no significant difference in the levels of serum cholesterol (control: 147±10 vs. simvastatin 161±5.2 mg/dl), creatinine and transaminases after treatment with simvastatin compared to control values.

Example 16

Effect of HMG-CoA Reductase Inhibitors on ecNOS Expression and Function in Mouse Aorta The activity of ecNOS in the aortae of simvastatin-treated (2 mg/kg) and saline-injected mice was determined by measuring the LNMA-inhibitable conversion of arginine to citrulline (FIG. 1A). The ecNOS activity in aortae from simvastatin-treated mice was significantly higher than in the control group (0.39±0.09 vs. 0.18±0.04 U/mg protein, n=8, p<0.05).

Figure 1B:
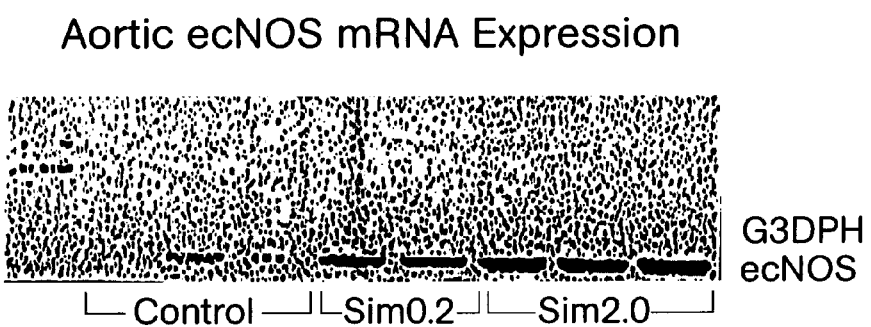

The ecNOS mRNA expression in the aortae of simvastatin-treated and -untreated mice was examined by quantitative RT-PCR (FIG. 1B). There was a significantly dose-dependent 3-fold increase of ecNOS message compared to that of GAPDH in simvastatin treated mice (n=3). These findings indicate that simvastatin upregulates ecNOS expression and activity in vivo.

Example 17

Effect of HMG-CoA Reductase Inhibitors on Cerebral Ischemia in Mice

Endothelium-derived NO protects against ischemic cerebral injury (Huang, Z et al., J Cereb Blood Flow Metab, 1996, 16:981–987). Therefore we examined, wether the observed upregulation of ecNOS by simvastatin in vivo has beneficial effects on cerebral infarct size. Following treatment for 14 days with 2 mg/kg of simvastatin, cerebral ischemia was produced by occluding the left middle cerebral artery for 2 hours. After 22 hours of reperfusion, mice were tested for neurological deficits using a well-established, standardized, observer-blinded protocol. The neurological motor deficit score improved in simvastatin-treated mice (n=18) by almost 2-fold compared to that of controls (n=12) (0.8±0.2 vs. 1.7±0.2, p<0.01).

Simvastatin-treated wild-type mice (n=18) had 25% smaller cerebral infarct sizes compared to untreated animals (73.8±8.5 mm3 vs. 100.7±7.3 mm3, n=12, p<0.05). This effect was concentration-dependent (0.2, 2, 20 mg/kg simvastatin), persisted for up to 3 days, and also occurred with lovastatin treatment, albeit at higher relative concentrations (data not shown). Furthermore, simvastatin increase cerebral blood flow by 23% and 35% over basal values at concentrations of 2 mg/kg and 20 mg/kg, respectively (n=8, p<0.05 for both). These findings suggest, that simvastatin decreases cerebral infarct size and neurological deficits.

Finally, to demonstrate that the reduction of cerebral infarct sizes by simvastatin is due to the upregulation of ecNOS, cerebral ischemia was applied to ecNOS mutant mice lacking ecNOS gene in the presence and absence of simvastatin (2 mg/kg, 14 days). There was no significant difference between the cerebral infarct sizes of simvastatin-treated and -untreated ecNOS mutant mice (n=6, p<0.05). These findings indicate that the upregulation of ecNOS mediates the beneficial effects of HMG-CoA reductase inhibitors on cerebral infarct size.

Example 18

Effect of HMG-CoA Reductase Inhibitors on ecNOS Expression in Mouse Brain

The ecNOS mRNA expression in the ischemic and contralateral (non-ischemic) hemispheres of mouse brain was examined by quantitative RT-PCR (FIG. 2) with respect to GAPDH mRNA levels. Simvastatin-treated mice (n=3) (2 mg/kg, 14 days) showed a 1.5- to 2-fold increase in ecNOS expression in the infarcted, ipsilateral hemisphere compared to the contralateral, non-infarcted side. In contrast, there was no difference in ecNOS expression in untreated mice between their infarcted and non-infacted hemispheres. These findings suggest that simvastatin may reduced cerebral infarct size by selectively increasing ecNOS expression in the ischemic and hypoxic infarct zone.

"Regulation of Endothelial Nitric Oxide Synthase Expression by Rho GTPases"

Experimental Procedures

Materials:

Mevastatin, farnesylpyrophosphate, geranylgeranylpyrophosphate, and L-mevalonate were purchased from Sigma Chemical Corp. (St. Louis, Mo.). Mevastatin (compactin- a HMG-CoA reductase inhibitor) was chemically activated by alkaline hydrolysis prior to use as previously described (Laufs, U et al., *J Biol Chem*, 1997, 272:31725–31729). FPT inhibitor I and -hydroxyfarnesylphosphonic acid were purchased from Calbiochem Corp. (La Jolla, Calif.). [a-$^{32}$P]CTP (3000 Ci/mmol) and [$^{35}$S]GTP S (1250 Ci/mmol) were supplied by New England Nuclear. The antibody detection kit (Enhanced Chemiluminescence) and the nylon nucleic acid (Hybond) and protein (PVDF) transfer membranes were purchased from Amersham Corp. (Arlington Heights, Ill.). The *Clostridium botulinum* C3 transferase was purchased from List Biological Laboratories, Inc. (Campbell, Calif.). Recombinant *Escherichia coli* cytotoxic necrotizing factor (CNF)-1 and RhoA mutants were kindly provided by K. Aktories (University of Freiberg, Germany) and W. Moolenaar (Netherlands Cancer Institute, Netherlands), respectively.

Cell Culture

Human endothelial cells were harvested using Type II collagenase (Worthington Biochemical Corp., Freehold, N.J.) as previously described (Laufs, U et al., *J Biol Chem*, 1997, 272:31725–31729; Liao, J K et al., *J Biol Chem*, 1995, 270:319–324). Cells of less than three passages were grown in a culture medium containing Medium 199, 20 mM HEPES, 50 mg/ml ECGS (Collaborative Research Inc., Bedford, Ma.), 100 mg/ml heparin sulfate, 5 mM L-glutamine (Gibco), 5% fetal calf serum (Hyclone, Logan, Utah), and antibiotic mixture of penicillin (100 U/ml)/streptomycin (100 mg/ml)/Fungizone (1.25 mg/ml). Confluent endothelial cells were used for all treatment conditions. For transfection studies, bovine aortic endothelial cells of less than 3 passages were cultured in a growth medium containing DMEM (Dulbecco's Modified Eagle's Medium), 5 mM of L-glutamine (Gibco), and 10% fetal calf serum. Cellular viability was determined by cell count, morphology, and trypan blue exclusion.

Preparation of LDL

The LDL was prepared as described earlier. The extent of LDL oxidation was estimated by assaying for thiobarbituric acid reactive substances (TBARS) and expressed as nanomoles of malondialdehyde per mg of LDL protein, as described earlier. Only freshly-isolated LDL with TBARS values of less than 0.5 nmol/mg was used in this study.

Western Blotting

Proteins were prepared and separated on SDS/PAGE as described earlier. Immuno-blotting was performed using monoclonal antibodies to ecNOS (1:400 dilution, Transduction Laboratories, Lexington, Ky.), to RhoA and RhoB (1:250 dilution, Santa Cruz Biotechnology Inc., Santa Cruz, Calif.), and to c-myc-tag (9E10, 1:200 dilution, Santa Cruz Biotechnology Inc.). Immunodetection was accomplished using a sheep anti-mouse secondary antibody (1:4000 dilution) or donkey anti-rabbit secondary antibody (1:4000 dilution) and the enhanced chemiluminescence (ECL) kit (Amersham Corp., Arlington Heights, Ill.). Autoradiography was performed as described earlier.

Assay for Rho GTP-binding Activity

The Rho GTP-binding activity was determined by immunoprecipitation of [$^{35}$S]GTP S-labeled Rho. Briefly, membrane and cytosolic proteins were isolated as previously desribed (Liao, J K and Homcy, C J, *J Clin Invest*, 1993, 92:2168–2172). Proteins (20 mg) from control and treated endothelial cells were incubated for 30 min at 37° C. in a buffer containing [$^{35}$S]GTP S (20 nM), GTP (2 mM), MgCl$_{22}$ (5 mM), EGTA (0.1 mM), NaCl (50 mM), creatinine phosphate (4 mM), phosphocreatinine kinase (5 units), ATP (0.1 mM), dithiothreitol (1 mM), leupeptin (100 mg/ml), aprotinin (50 mg/ml), and phenylmethanesulfonyl fluoride (PMSF, 2 mM). The assay was terminated with excess unlabeled GTP S (100 mM).

Samples were then resuspended in 100 ml of immunopricipitation buffer containing Triton-X (1%), SDS (0.1%), NaCl (150 mM), EDTA (5 mM), Tris-HCl (25 mM, pH 7.4), leupeptin (10 mg/ml), aprotinin (10 mg/ml), and PMSF (2 mM). The RhoA or RhoB antisera were added to the mixture at a final dilution of 1:75. The samples were allowed to incubate for 16 h at 4° C. with gentle mixing. The antibody-G-protein complexes were then incubated with 50 ml of protein A-Sepharose (1 mg/ml, Pharmacia Biotech Inc.) for 2 h at 4° C., and the immuno-precipitate was collected by centrifugation at 12,000×g for 10 min.

Preliminary studies using Western analysis of the supernatant indicated that both RhoA and RhoB were completely immunoprecipitated under these conditions. The pellets were washed four times in a buffer containing HEPES (50 mM, pH 7.4), NaF (100 mM), sodium phosphate (50 mM), NaCl (100 mM), Triton X-100 (1%), and SDS (0.1%). The final pellet containing the immunoprecipitated [$^{35}$S]GTP S-labeled Rho proteins was counted in a liquid scintillation counter (LS 1800, Beckman Instruments, Inc. Fullerton, Calif.). Nonspecific activity was determined in the presence of excess unlabeled GTP S (100 mM).

Overexpression of Rho Mutants

For transfection studies, bovine rather than human endothelial cells were used because of their higher transfection efficiency by the calcium-phosphate precipitation method (12% vs <4%) (15). Bovine endothelial cells (60–70% confluent) were transfected with 15 mg of the indicated cDNAs: the insertless vector (pcDNA3), pcDNA3-c-myc-wtRhoA (wildtype RhoA), and pcDNA3-c-myc-N19RhoA (dominant-negative RhoA mutant) (Gebbink, M et al., *J Cell Biol*, 1997, 137:1603–1613). As an internal control for transfection efficiency, pCMV. b-Gal plasmid (5 mg) was co-transfected. Preliminary results using b-galactosidase staining indicate that cellular transfection efficiency was approximately 10% to 14%. The b-galactosidase activity was determined by a chemiluminescence assay (Dual-Light, Tropix, Bedford, Ma.) using a Berthold L9501 luminometer. Approximately 24 h after transfection, cells were harvested for immunoblot analyses of ecNOS expression. The ecNOS protein levels were then standardized to the corresponding levels of transfected RhoA expression as determined by antisera to the corresponding c-myc tag.

Assay for ecNOS Activity

The ecNOS activity was determined by a modified nitrite assay as previously described. Briefly, endothelial cells grown in phenol-free medium were exposed to C3 transferase (50 mg/ml), FPP (10 mM), GGPP (5 mM), CNF-1 (200 ng/ml), or mevastatin (10 mM). After 24 h, conditioned medium (300 ml) was mixed with 30 ml of freshly-prepared 2,3-diaminonaphthalene (1.5 mM of DAN in 1 M of HCl). The mixture was protected from light and incubated at 20° C. for 10 min. The reaction was terminated with 15 ml of 2.8 M of NaOH. Fluorescence of 1-(H)-naphthotriazole was measured with excitation and emission wavelengths of 365 and 450 nm, respectively. Standard curves were constructed with known amounts of sodium nitrite. Nonspecific fluorescence was determined in the presence of LNMA (3 mM). Previous studies with nitrate reductase indicate that the nitrite to nitrate concentration in the medium was approximately 5:1 and that this ratio did not vary under the described treatment conditions (Laufs, U et al., *J Biol Chem*, 1997, 272:31725–31729).

Data Analysis

Band intensities from Northern and Western blots were analyzed as described earlier. Paired and unpaired Student's t-tests were employed to determine the significance of changes in densitometric measurements, GTP-binding activities, and nitrite levels. A significant difference was taken for $p<0.05$.

Example 19

Cell Culture

Relatively pure (>98%) human saphenous vein endothelial cell cultures were confirmed by their morphological features (i.e. cuboidal, cobble-stone, contact inhibited) using phase-contrast microscopy and immunofluorescent-staining with antibodies to Factor VIII (data not shown). There were no observable adverse effects of mevastatin, FPP, GGPP, C3 transferase, and CNF-1 on cellular viability. However, higher concentrations of mevastatin (>50 mM) or CNF-1 (>5 mg/ml) did produce cytotoxicity and therefore were not used. Cellular confluency and viability as determined by light microscopy and trypan blue exclusion were maintained for all treatment conditions described.

Example 20

Effects of Isoprenoid Intermediates on ecNOS mRNA Expression

Figure 3A:
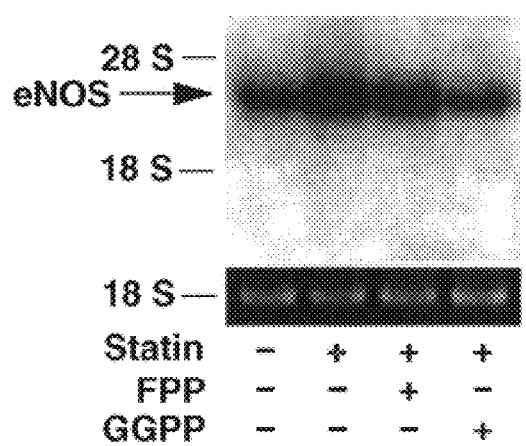
FIG. 3. Northern blots showing the effects of mevastatin alone (FIG. 3A) or in combination (FIG. 3B) with FPP or GGPP on eNOS (ecNOS) steady-state mRNA levels after 24 h.

We have shown that inhibition of endothelial HMG-CoA reductase by lovastatin or simvastatin upregulates ecNOS expression and activity via increases in ecNOS mRNA stability (Examples 3–8 and Laufs, U et al., *J Biol Chem*, 1997, 272:31725–31729). Similarly, treatment of endothelial cells with mevastatin (10 mM) increased ecNOS steady-state mRNA levels by 405±15% after 24 h (FIG. 3A). On a molar basis, we find that mevastatin is equally potent compared with lovastatin but approximately ten times less potent compared to simvastatin. This is consistent with their relative $IC_{50}$ values for HMG-CoA reductase inhibition (Blum, C B, *Am. J Cardiol*, 1994, 73:3D–11D).

Figure 3B:
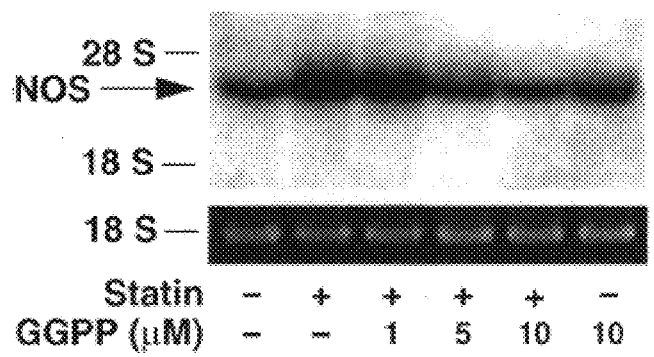

To determine which downstream isoprenoid intermediate in the cholesterol biosynthetic pathway regulates ecNOS expression, endothelial cells were treated with mevastatin (10 mM) in the presence or absence of isoprenoid intermediates, geranylgeranylpyrophosphate (GGPP) or farnesylpyrophosphate (FPP). Co-treatment with FPP (10 mM) mildly reduced ecNOS mRNA levels compared to mevastatin alone. However, co-treatment with GGPP (10 mM) completely reversed the upregulation of ecNOS mRNA levels by mevastatin. In a concentration-dependent manner, GGPP reversed the effects of mevastatin (10 mM) with complete reversal occuring at a GGPP concentration of 5 mM (FIG. 3B). Interestingly, treatment with GGPP (10 mM) alone did not significantly affect basal ecNOS mRNA levels.

Figure 4:
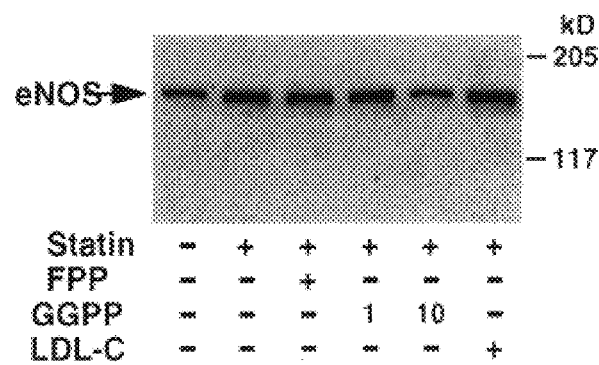
FIG. 4. Western blots showing the effects of mevastatin alone or in combination with FPP or GGPP or LDL-cholesterol on eNOS (ecNOS) protein levels after 24 h.

Similarly, treatment with mevastatin (10 mM) increased ecNOS protein levels by 180±11% after 24 h ($p<0.05$, n=4) (FIG. 4). Co-treatment with FPP (10 mM) or LDL (1 mg/ml) did not significantly reverse the effects of mevastatin on ecNOS protein levels. Furthermore, inhibition of protein farnesyltransferase with the farnesyl-protein transferase inhibitor I (0.5–50 mM) or -hydroxyfarnesylphosphonic acid (2–20 mM) did not affect ecNOS protein levels. In contrast, co-treatment with GGPP at a concentration of 10 mM, but not 1 mM, completely reversed the upregulation of ecNOS protein levels by mevastatin. These findings indicate that ecNOS expression is negatively regulated by geranylgeraniol synthesis.

Example 21

Effects of Mevastatin on Rho Membrane Translocation

The geranylgeranylation of the small GTPases, RhoA and RhoB, are essential for their membrane translocation from the cytosol (Van Aelst, L and D' Souza-Schorey, C, *Genes Dev*, 1997, 11:2295–2322). Under basal culture conditions, both RhoA and RhoB are present in the membranes and cytosol. Treatment with mevastatin decreased membrane localization of RhoA and RhoB by 60±5% and 78±6% and produce a concomitant increase in RhoA and RhoB in the cytosol by 65±4 % and 87±7 %. Co-treatment with GGPP (5 mM), but not FPP (10 mM) reversed the effects of mevastatin and completely restored the amount of cytosolic and membrane-asociated RhoA and RhoB to basal levels. These findings suggest that inhibition of Rho geranylgeranylation by mevastatin prevents RhoA and RhoB from translocating to and associating with the cellular membrane.

Example 22

Effects of Mevastatin on Rho GTP-binding Activity

To determine whether geranylgeranylation of RhoA and RhoB affects their activity (i.e. GTP-bound state), we immunoprecipitated [$^{35}$S]GTP S-labeled RhoA and RhoB from the membrane and cytosol of endothelial cells treated with mevastatin (10 mM) in the presence of GGPP (5 mM) or FPP (10 mM). Under basal conditions, endothelial cells have membrane-associated RhoA and RhoB activity of 4.4±0.1 fmol/mg/min and 3.8±0.4 fmol/mg/min, respectively. Treatment with mevastatin decreased membrane-associated RhoA and RhoB GTP-binding activity by 52% (2.1±0.4 fmol/mg/min; $p<0.01$) and 37% (2.4±0.6 fmol/mg/min; $p<0.05$), respectively (n=3).

Co-treatment with FPP (10 mM) produced no significant effects on RhoA and RhoB GTP-binding activity compared to mevastatin alone (2.6±0.9 fmol/mg/min and 2.7±0.5 fmol/mg/min, respectively, $p>0.05$, n=3). However, co-treatment with GGPP (10 mM) completely reversed the inhibitory effects of mevastatin on RhoA and RhoB GTP-binding activity (4.1±0.3 fmol/mg/min and 3.6±0.5 fmol/mg/min, respectively, $p<0.05$, n=3). Cytosolic RhoA and RhoB were relatively inactive (i.e. <1 fmol/mg/min) and their activities were not affected by treatment with mevastatin alone or in combination with GGPP or FPP. Taken together, these results indicate that geranylgeranylation of RhoA and RhoB is necessary for their membrane translocation and that membrane-associated Rho is relatively more active in terms of GTP-binding than cytosolic Rho.

Example 23

Effects of C3 Transferase on ecNOS Expression

To determine whether the inhibition of Rho mediates the effects of mevastatin on ecNOS expression, endothelial cells were treated with mevastatin in the presence and absence of *Clostridium botulinum* C3 transferase (5–50 mg/ml), an exoenzyme which specifically inactivates Rho by ADP-ribosylation (Aktories, K, *J Clin Invest*, 1997, 12:S1 1-S1 3). Treatment of endothelial cells with mevastatin (10 mM) or C3 transferase (50 mg/ml) for 48 h augmented ecNOS protein levels by 260±9% and 250±10%, respectively (p<0.01, n=3). Lower concentrations of C3 transferase (i.e. <50 mg/ml) produced correspondingly smaller increases in ecNOS expression (data not shown). In contrast to the effect of mevastatin, the stimulatory effect of C3 transferase on ecNOS expression was not reversed in the presence of L-mevalonate (200 mM).

Example 24

Effects of Dominant-negative RhoA on ecNOS Expression

Figure 6:
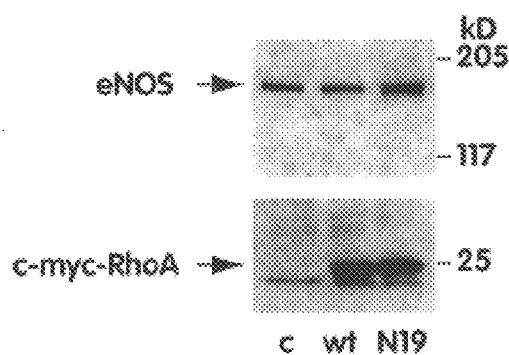
FIG. 6. Western blots showing eNOS (ecNOS) protein levels after transfection with insertless vector, pcDNA3 (C), c-myc-wildtype-RhoA (wt), and c-myc-N19RhoA (dominant-negative rhoA mutant).

Bovine aortic endothelial cells were transfected with insertless pcDNA3 vector, c-myc-tagged wildtype RhoA (wtRhoA), or c-myc-tagged dominant-negative RhoA mutant (N19RhoA) which cannot exchange GDP for GTP and therefore is inactive (Gebbink, M et al., *J Cell Biol*, 1997, 137:1603–1613). Immunostaining for b-galactosidase activity demonstrate comparable transfection efficiency of approximately 10% among the RhoA constructs and between treatment conditions. To distinguish between transfected and endogenous RhoA, the amount of transfected RhoA constructs expressed was assessed by immunoblotting using an antibody to c-myc (9E 10), which recognizes a 21 kD band only in wtRhoA and N19RhoA transfected cells (FIG. 6).

Overexpression of wtRhoA mildly reduced basal ecNOS protein expression by 15±4% suggesting that increased RhoA expression results in a decrease in basal ecNOS expression (p<0.05, n=3). Endothelial cells transfected with the dominant-negative N19RhoA mutant to comparable levels as wtRhoA as assessed by the amount of c-myc-tag, however, exhibited a 150±5% increase in ecNOS protein levels (p<0.05, n=3). The observed effects of N19RhoA overexpression on overall ecNOS protein levels (i.e. transfected and non-transfected cells) are more profound when one considers that only 10% of the endothelial cells were actually transfected. These findings are consistent with our earlier findings that inhibition of Rho GTPase activity leads to an increase in ecNOS expression.

Example 25

Effects of CNF-1 on ecNOS Expression

The *Escherichia coli* cytotoxic necrotizing factor (CNF)-1 is known to directly and specifically activate rho proteins via glutamine deamination (Aktories, K, *J Clin Invest*, 1997, 12:S11–S13; Schmidt, G et al., *Nature*, 1997, 387:725–729; Flatau, G et al., *Nature*, 1997, 387:729–733). Treatment of endothelial cells with mevastatin (10 mM) increased ecNOS mRNA levels by 390±15% compared to basal levels (p<0.01, n=3). Co-treatment with CNF-1 (200 ng/ml) completely reversed the upregulation of ecNOS mRNA by mevastatin (p>0.05 compared to basal levels, n=3). Treatment with CNF-1 (200 ng/ml) alone, however, decreased ecNOS steady-state mRNA levels to 48±6% of basal levels at 24 h (p<0.05, n=3). These findings indicate that the direct activation of Rho leads to the downregulation of ecNOS expression.

Example 26

Effects of HMG-CoA Reductase Inhibitors and Rho on ecNOS Activity

Figure 7:
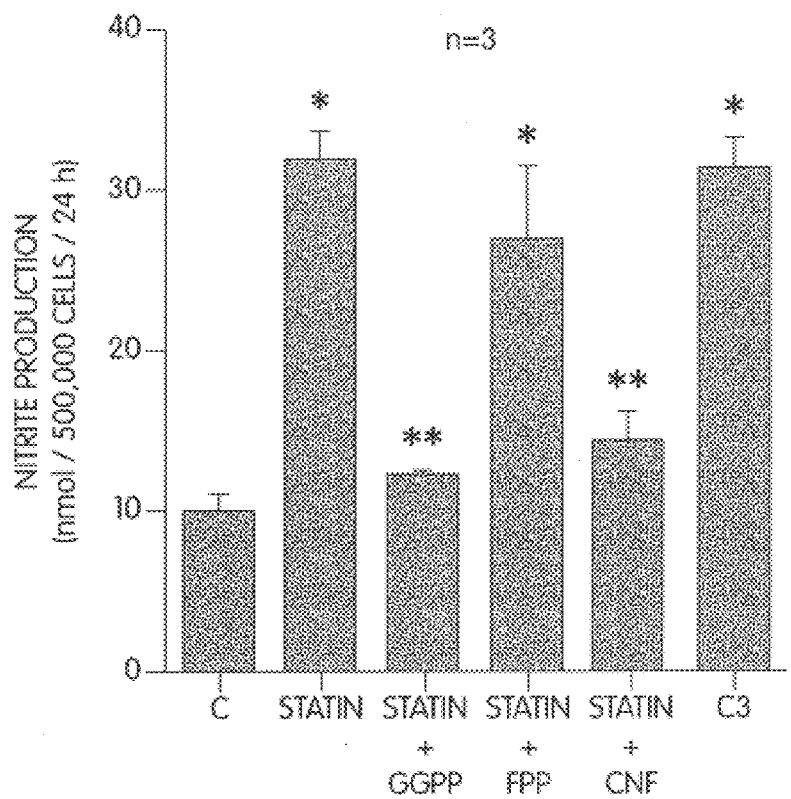
FIG. 7. Effects of C3 transferase, FPP, GGPP, and CNF-1 on mevastatin-induced eNOS (ecNOS) activity as determined by LNMA-inhibitable nitrite production at 24 h.

The ecNOS activity was assessed by measuring the LNMA-inhibitable nitrite accumulation in conditioned media of endothelial cells (Laufs, U et al., *J Biol Chem*, 1997, 272:31725–31729). Basal ecNOS activity was 9.7±1.4 nmol/500,000 cells/24 hours (FIG. 7). Treatment of endothelial cells with mevastatin (10 mM) resulted in a 3-fold increase in nitrite accumulation (32±1.9 nmol/500,000 cells/24 hours, p<0.01). This increase in ecNOS activity by mevastatin was reversed by co-treatment with GGPP (5 mM), but not FPP (10 mM) (12±0.8 and 27±4.9 nmol/500,000 cells/24 hours, respectively). Furthermore, direct activation of Rho by CNF-1 (200 ng/ml) reversed mevastatin-induced increase in ecNOS activity (32±1.9 to 14±2.1 nmol/500,000 cells/24 hours, p<0.05). In contrast, inhibition Rho by C3 transferase (50 mg/ml) resulted in a 3-fold increase in nitrite accumulation (31±2.1 and ±nmol/500,000 cells/24 hours, p<0.05). These results indicate that Rho not only negatively regulates ecNOS expression, but also ecNOS activity.

"Regulation of Endothelial Nitric Oxide Synthase Activity by Agents that Disrupt Actin Cytoskeletal Organization"

Experimental Procedures

Materials:

Myosin light chain kinase inhibitors BDM [2,3-butanedione 2-monoxime], ML-7 [1-(5-iodonaphthalene-1-sulphonyl)-1 H-hexahydro-1,4-diazepine hydrochloride], and H-7 [1-(5-isoquinolinesulphonyl)-2-methylpiperazine dihydro-chloride], were purchased from Sigma Chemical Corp. (St. Louis, Mo.). Nocodazole {Methyl-(5-[2-thienylcarbonyl]-1H-benzimidazol -2-yl)carbamate} was also purchased from Sigma.

Cell culture, Western blotting and Northern blotting were performed as described earlier.

Example 27

Figure 8:
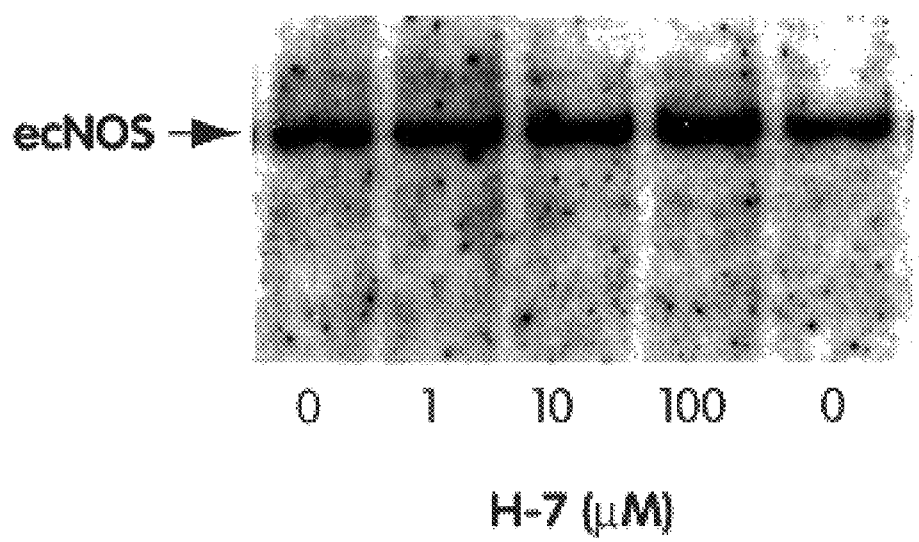
FIG. 8. Immunoblots showing the concentration-dependent effects of MLC kinase inhibitor H-7 on ecNOS protein levels after 24 hours.

Effects of Agents That Disrupt Actin Cytoskeletal Organization on ecNOS Protein and mRNA Expression To determine whether downstream targets of rhoGTPase exert any effect on ecNOS expression, endothelial cells were treated in the presence and absence of a myosin light chain (MLC) kinase inhibitor, for example, H-7. MLC kinase inhibitors decrease MLC phosphorylation and stress fiber formation. Treatment of endothelial cells with H-7 (1–100 mM) for 24 hours augmented ecNOS protein levels (FIG. 8). Similar experiments using a different MLC kinase inhibitor (ML-7), produced identical results.

Figure 9:
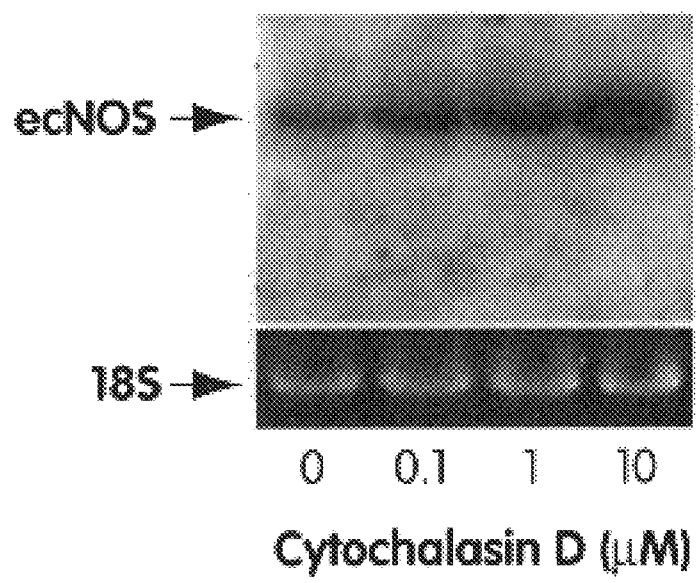
FIG. 9. Northern blots showing ecNOS expression of endothelial cells treated with cytochalasin D at 24 hours.
Figure 10:
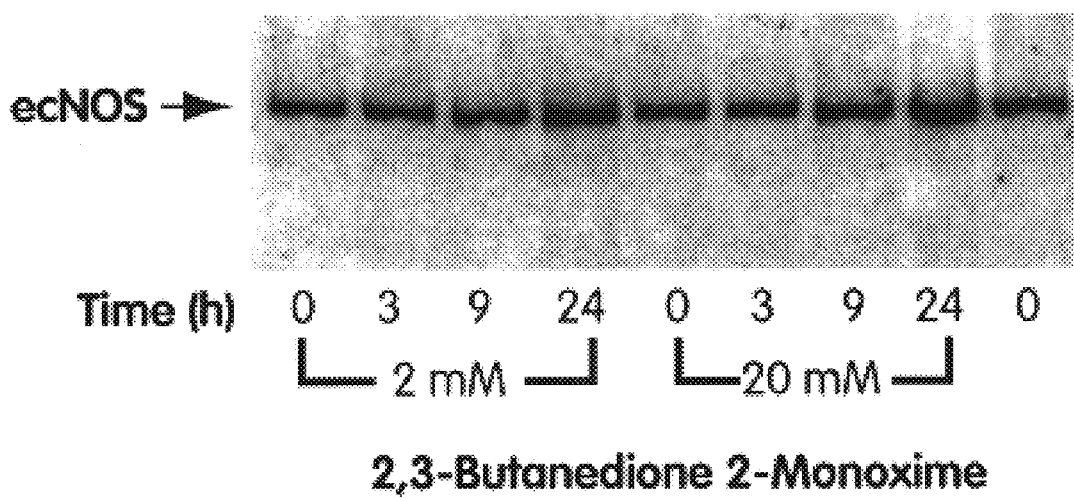
FIG. 10. Immunoblots showing the concentration-dependent effects of 2,3-butanedione 2-monoxime on ecNOS protein levels.

Furthermore, disruption of the actin cytoskeletal organization by Cytochalasin D (an agent that interferes with actin polymerization) or BDM (a different MLC kinase inhibitor), also lead to upregulation of ecNOS (FIGS. 9 and 10 respectively).

Figure 11:
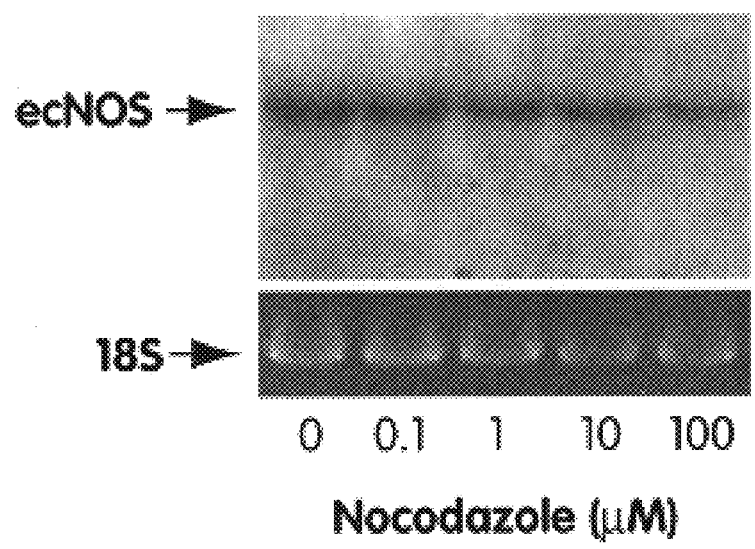
FIG. 11. Northern blots showing ecNOS expression of endothelial cells treated with nocodazole for 24 hours.

Inhibition, however, of cell cycle progression by anaphicoline (data not shown) or disruption of the microtubular cytoskeleton by enhancing microtubule depolymerization with nocodazole, do not increase ecNOS expression (FIG. 11).

These findings show that the uregulation of ecNOS expression is relatively specific to disruption of the actin cytoskeleton. Additionally, the increased ecNOS expression by Cytochalasin D or BDM does not result from nonspecific cytotoxicity of these agents.

DETAILED DESCRIPTION OF THE INVENTION

FIG. 1. A) NOS-Activity measured by (C14)-arginine-citrulline assay in the aortas of wild type SV-129 mice after treatment with simvastatin (Sim, 2 mg/kg, s.c., 14 days) and of mice injected with PBS (Control), n=8, p<0.05.

B) ecNOS mRNA expression determined by quantitative polymerase chain reaction in wild-type SV-129 mice aortas after treatment with simvastatin (Sim0.2, 0.2 mg/kg, s.c. and Sim20, 20 mg/kg, s.c.) for 14 days and of mice injected with saline (Control) in comparison to glyceraldehyde 3-phosphate dehydrogenase (G3DPH) mRNA expression.

ecNOS expression and function is upregulated in the aortas of mice treated with Sim.

Figure 2:
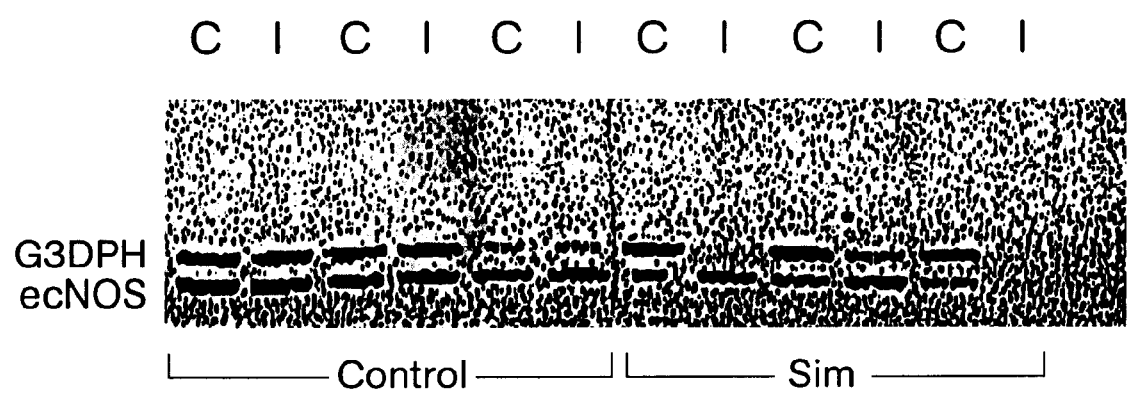
FIG. 2. ecNOS mRNA expression in the infarcted, ipsolateral (I) and not-infarcted, contralateral (C) forebrain hemispheres of SV-129 mice with and without treatment with simvastatin.

FIG. 2. ecNOS mRNA expression in the infarcted, ipsolateral (I) and not-infarcted, contralateral (C) forebrain hemispheres of SV-129 mice after treatment with simvastatin (Sim, 2 mg/kg, s.c., 14 days) and mice injected with saline (Control), as determined by quantitative polymerase chain reaction compared to glyceraldehyde 3-phosphate dehydrogenase (G3DPH) mRNA expression. ecNOS mRNA expression was upregulated in the infarcted brain area in Sim-treated animals.

FIG. 3. A) Northern analyses (20 mg total RNA/lane) showing the effects of mevastatin (Statin, 10 mM) alone or in combination with FPP (10 mM) or GGPP (10 mM) on eNOS steady-state mRNA levels at 24 h. B) Concentration-dependent effects of GGPP (1–10 mM) on mevastatin (10 mM)-induced increases in eNOS mRNA levels after 24 h. Each experiment was performed three times with comparable results. The corresponding ethidium bromide-stained 28S band intensities were used to standardize loading conditions.

FIG. 4. Immunoblots (30 mg protein/lane) showing the effects of mevastatin (Statin, 10 mM) alone or in combination with FPP (10 mM), GGPP (1–10 mM), or LDL cholesterol (LDL-C, 1 mg/ml) on eNOS protein levels after 24 h. The blot is representative of three separate experiments.

Figure 5:
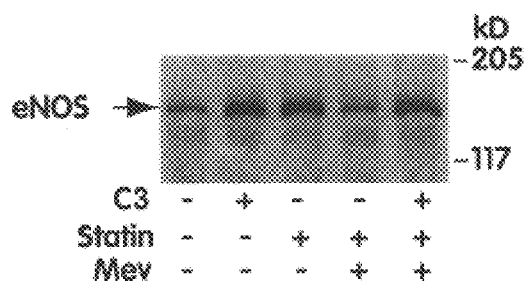
FIG. 5. Western blots showing the effects of C3 transferase, mevastatin, or L-mevalonate on eNOS (ecNOS) protein levels after 24 h.

FIG. 5. Immunoblot (30 mg protein/lane) showing the effects of C3 transferase (C3, 50 mg/ml), mevastatin (Statin, 10 mM), or L-mevalonate (Mev, 200 mM) on eNOS protein levels after 48 h. The blot is representative of three separate experiments.

FIG. 6. Immunoblots (30 mg protein/lane) showing eNOS protein levels after transfection with insertless vector, pcDNA3 (C), c-myc-wildtype-RhoA (wt), and c-myc-N19RhoA (dominant-negative rhoA mutant). The levels of overexpressed RhoA mutants were determined by immunoblotting for their corresponding c-myc-tags (c-myc-RhoA). Experiments were performed three times with similar results.

FIG. 7. Effects of C3 transferase (C3, 50 mg/ml), FPP (10 mM), GGPP (5 mM), and CNF-1 (200 ng/ml) on mevastatin (Statin, 10 mM)-induced eNOS activity as determined by LNMA-inhibitable nitrite production at 24 h. Experiments were performed three times in duplicate with less than 5% variation. *p<0.05 compared with control (C), **p<0.05 compared with mevastatin.

FIG. 8. Immunoblots (30 mg protein/lane) showing the concentration-dependent effects of MLC kinase inhibitor H-7on ecNOS protein levels after 24 hours.

FIG. 9. Northern blot analysis (20 mg total RNA/lane) showing ecNOS mRNA expression of endothelial cells treated with cytochalasin D at 24 hours.

FIG. 10. Immunoblots (30 mg protein/lane) showing the concentration-dependent effects of 2, 3-butanedione 2-monoxime on ecNOS protein levels.

FIG. 11. Northern blot analysis (20 mg total RNA/lane) showing ecNOS mRNA expression of endothelial cells treated with nocodazole for 24 hours.

EQUIVALENTS

Those skilled in the art will recognize, or be able to ascertain using no more than routine experimentation, many equivalents to the specific embodiments of the invention described herein. Such equivalents are intended to be encompassed by the following claims. A Sequence Listing follows the claims.

All references disclosed herein are incorporated by reference in their entirety.

What is claimed is:

1. A method for reducing brain injury resulting from a stroke comprising:

administering to a subject having experienced an ischemic stroke or having an abnormally high risk of an ischemic stroke, an agent that disrupts actin cytoskeletal organization in an amount effective to increase endothelial cell Nitric Oxide Synthase activity in the brain tissue of the subject, provided that the agent that disrupts actin cytoskeletal organization is not an agent selected from the group consisting of a rho GTPase function inhibitor, a cytochalasin, and an isoquinoline sulphonyl compound.

2. The method of claim 1, wherein the agent that disrupts actin cytoskeletal organization is administered prophylactically to a subject having an abnormally high risk of an ischemic stroke.

3. The method of claim 1, wherein the agent that disrupts actin cytoskeletal organization is administered acutely to a subject having experienced an ischemic stroke.

4. The method of claim 1, wherein the agent that disrupts actin cytoskeletal organization is selected from the group consisting of a myosin light chain kinase inhibitor, a myosin light chain phosphatase, a protein kinase N inhibitor, and a phospatidylinositol 4-phosphate 5-kinase inhibitor.

5. The method of claim 4, wherein the myosin light chain kinase inhibitor is selected from the group consisting of 2,3-butanedione-2-monoxime, 1-(5-iodonaphthalene-1-sulphonyl)-1H-hexahydro-1,4-diazepine hydrochloride, 1-(5-iodonaphthalene-1-sulphonyl)-1H-hexahydro-1,4-diazepine hydrochloride, 1-(5-chloronaphthalene-1-sulfonyl)-1H-hexahydro-1,4-diazepine hydrochloride, wortmannin, N-(6-Aminohexyl)-5-chloro-1-naphthalenesulfonamide, and N-(6-Aminoethyl)-5-chloro-1-naphthalenesulfonamide.

6. The method of claim 1, further comprising co-administering a substrate of endothelial cell Nitric Oxide Synthase.

7. The method of claim 6, wherein the substrate of endothelial cell Nitric Oxide Synthase is L-arginine.

8. The method of claim 1, further comprising co-administering an agent other than an agent that disrupts actin cytoskeletal organization that increases endothelial cell Nitric Oxide Synthase activity.

9. The method of claim 1, further comprising co-administering at least one different agent that disrupts actin cytoskeletal organization in an amount effective to increase endothelial cell Nitric Oxide Synthase activity in said tissue of the subject.

* * * * *